United States Patent
Rolland

(10) Patent No.: US 7,862,804 B2
(45) Date of Patent: *Jan. 4, 2011

(54) ADMISTRATION OF C-GLYCOSIDE COMPOUNDS FOR DEPIGMENTING/WHITENING THE SKIN

(75) Inventor: Anne Rolland, Paris (FR)

(73) Assignee: Loreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/545,581

(22) Filed: Oct. 11, 2006

(65) Prior Publication Data

US 2007/0081956 A1    Apr. 12, 2007

(30) Foreign Application Priority Data

Oct. 11, 2005  (FR)  .................................. 05 53080
Jul. 3, 2006   (FR)  .................................. 06 52774

(51) Int. Cl.
*A61K 8/00*   (2006.01)
*A61K 31/70*  (2006.01)
*A01N 43/04*  (2006.01)

(52) U.S. Cl. ............................. 424/62; 514/8; 514/23; 514/24; 514/42; 514/62; 435/85; 424/401; 424/70.13

(58) Field of Classification Search .................. None
See application file for complete search history.

(56) References Cited

U.S. PATENT DOCUMENTS 4,454,123 A   6/1984  Noyori et al.
5,310,730 A   5/1994  Fujinuma et al.
5,786,469 A   7/1998  Lavaire et al.
5,882,658 A   3/1999  Simon et al.
2004/0048785 A1* 3/2004 Dalko et al. .................. 514/8

FOREIGN PATENT DOCUMENTS

EP   0 754 449 A1      1/1997
WO   WO 02/051828 A2   7/2002
WO   WO 02/051828 A3   7/2002

OTHER PUBLICATIONS

Nordlund, James; Boissy, Raymond; Hearing, Vincent; King, Richard; Oetting, William; Ortonne, Jean-Paul; The Pigmentary System, Apr. 25, 2006, Blackwell Publishing, pp. 829-836.*
Vippagunta, Sudha R.; Brittain, Harry G.; Grant, David J.W.; Crystalline Solids, 2001, Elsevier; vol. 48, pp. 3-26.*
Definition for: liver spot. (n.d.). The American Heritage® Dictionary of the English Language, Fourth Edition., 2004, Houghton Mifflin Co.; Retrieved Oct. 21, 2009, from Dictionary.com website: <http://dictionary.reference.com/browse/liver spot>, p. 1.*
French Search Report corresponding to FR 05/53080, issued Jul. 10, 2006, 2 pages.

* cited by examiner

*Primary Examiner*—Yvonne L Eyler
*Assistant Examiner*—Ivan Greene
(74) *Attorney, Agent, or Firm*—Buchanan, Ingersoll & Rooney PC

(57) ABSTRACT

C-glycoside compounds having the formula (I):

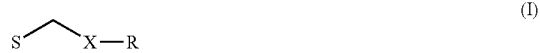

are useful for depigmenting/whitening the skin and/or for the anti-browning thereof.

47 Claims, No Drawings

ADMINISTRATION OF C-GLYCOSIDE COMPOUNDS FOR DEPIGMENTING/WHITENING THE SKIN

CROSS-REFERENCE TO PRIORITY APPLICATIONS

This application claims priority under 35 U.S.C. §119 of FR 05/53080, filed Oct. 11, 2005 and FR 06/52774, filed Jul. 3, 2006, each hereby expressly incorporated by reference and each assigned to the assignee hereof.

BACKGROUND OF THE INVENTION

1. Technical Field of the Invention

The present invention relates to the administration of C-glycoside compounds for depigmenting and/or whitening the skin.

2. Description of Background and/or Related and/or Prior Art

The color of human skin depends on various factors, in particular on the seasons of the year, race and sex, and it is mainly determined by the nature and the concentration of melanin produced by the melanocytes. Melanocytes are specialized cells which synthesize melanin via specific organelles, the melanosomes. In addition, at different periods in their lives, certain individuals witness the appearance on the skin and more especially on the hands of darker and/or more highly colored blemishes which give the skin a heterogeneous appearance. These blemishes are also due to a high concentration of melanin in the keratinocytes situated at the surface of the skin.

The use of inoffensive topical depigmenting substances which are highly effective is very particularly sought with a view to treating regional hyperpigmentations by melanocytic hyperactivity, such as idiopathic melasmas, arising during pregnancy ("mask of pregnancy" or chloasma) or oestrone/progestogen contraception, localized hyperpigmentation by benign melanocytic hyperactivity and proliferation, such as senile pigment blemishes known as actinic lentigines, accidental hyperpigmentations, possibly due to photosensitization or to post-lesional healing, as well as certain leucodermas, such as vitiligo. For the latter conditions (healing of which can result in a scar giving the skin a whiter appearance), for want of being able to repigment the damaged skin, the end result is to depigment the remaining normal skin regions to give the whole skin a homogeneous white coloring.

The mechanism of formation of the pigmentation of the skin, that is to say of the formation of melanin, is particularly complex and involves, schematically, the following main stages:

Tyrosine→Dopa→Dopaquinone→Dopachrome→Melanin

Tyrosinase (monophenol dihydroxyl phenylalanine:oxygen oxidoreductase EC 1.14.18.1) is the essential enzyme involved in this sequence of reactions. In particular, it catalyzes the conversion reaction of tyrosine to give Dopa (dihydroxyphenylalanine), by virtue of its hydroxylase activity, and the conversion reaction of Dopa to give dopaquinone, by virtue of its oxidase activity. This tyrosinase only acts when it is in the maturation state under the effect of certain biological factors.

The depigmenting substances can act directly on the vitality of the epidermal melanocytes where melanogenesis takes place and/or interfere with one of the stages in the biosynthesis of melanin, either by inhibiting one of the enzymes involved in melanogenesis or by being inserted as structural analogue of one of the chemical compounds in the sequence for the synthesis of melanin, which sequence can then be blocked and thus ensure depigmentation.

The substances most commonly used as depigmenting agents are more particularly hydroquinone and its derivatives, in particular its ethers, such as hydroquinone monomethyl ether and monoethyl ether. These compounds can, however, produce undesirable effects, such as the appearance of red skin blotches, in specific situations, such as use at high concentrations, sensitive skin or skin exhibiting a dermatological disorder, and the like.

Furthermore, use is commonly made, as inhibitor of the activation of tyrosinase, of kojic acid, which complexes the copper present in the active site of this enzyme. However, this compound can prove to be unstable in solution, which complicates its formulation.

Thus, need continues to exist for novel whitening agents for human skin with an action as effective as those known to the art and which are non-irritating, non-toxic and/or non-allergizing for the skin while being stable in a composition, or else alternatively which have a reinforced action, so as to be able to be administered in a smaller amount, which greatly reduces any side effects.

SUMMARY OF THE INVENTION

It has now surprisingly and unexpectedly been determined that certain C-glycoside compounds exhibit a good depigmenting activity without exhibiting cytotoxicity.

C-Glycosides are described in EP-1-345,919 as having the property of inducing the synthesis of proteoglycans and of glycosaminoglycans, thus contributing to reinforcing the extracellular matrix of the dermis.

More specifically, the present invention thus features the cosmetic or pharmaceutical, in particularly dermatological, administration, whether regime or regimen, of at least one compound having the following formula (I):

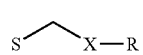

(I)

in which:
R is:
a saturated linear $C_1$ to $C_{20}$, in particular $C_1$ to $C_{10}$, alkyl radical, an unsaturated linear $C_2$ to $C_{20}$, in particular $C_2$ to $C_{10}$, alkyl radical or a saturated or unsaturated and branched or cyclic $C_3$ to $C_{20}$, in particular $C_3$ to $C_{10}$, alkyl radical, with the exception of a substituted phenyl radical;
a saturated linear $C_1$ to $C_{20}$, in particular $C_1$ to $C_{10}$, hydrofluoro- or perfluoroalkyl radical, an unsaturated linear $C_2$ to $C_{20}$, in particular $C_2$ to $C_{10}$, hydrofluoro- or perfluoroalkyl radical or a saturated or unsaturated and branched or cyclic $C_3$ to $C_{20}$, in particular $C_3$ to $C_{10}$, hydrofluoro- or perfluoroalkyl radical;

with the proviso that the hydrocarbon chain constituting said radicals may be interrupted by 1, 2, 3 or more heteroatoms selected from among:
an oxygen atom,
a sulfur atom,
a nitrogen atom, and
a silicon atom, and with the further proviso that the hydrocarbon chain constituting said radicals may optionally be substituted by at least one radical selected from among:

—$OR_4$,
—$SR_4$,
—$NR_4R_5$,
—$COOR_4$,
—$CONHR_4$,
—CN,
a halogen atom,
a $C_1$ to $C_6$ hydrofluoro- or perfluoroalkyl radical,
a $C_3$ to $C_8$ cycloalkyl radical, and/or wherein $R_4$ and $R_5$ represent, independently of one another, a hydrogen atom, a saturated linear $C_1$ to $C_{30}$, in particular $C_1$ to $C_{12}$, alkyl, perfluoroalkyl or hydrofluoroalkyl radical, an unsaturated linear $C_2$ to $C_{30}$, in particular $C_2$ to $C_{12}$, alkyl, perfluoroalkyl or hydrofluoroalkyl radical, a saturated or unsaturated and branched or cyclic $C_3$ to $C_{30}$, in particular $C_3$ to $C_{12}$, alkyl, perfluoroalkyl or hydrofluoroalkyl radical, or a $C_6$ to $C_{10}$ aryl radical;

X is a radical selected from among the following:

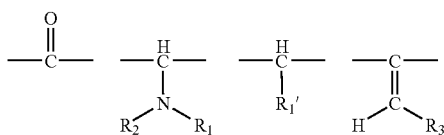

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;

S is a monosaccharide or a polysaccharide having up to 20 sugar units, in particular up to 6 sugar units, in a pyranose and/or furanose form and of the L and/or D series, with the proviso that said mono- or polysaccharide may be substituted by a necessarily free hydroxyl group and optionally one or more optionally protected amine functional group(s), and the S—$CH_2$—X bond is a bond of C-anomeric nature which can be α or β, and the cosmetically acceptable salts, solvates, hydrates and isomers thereof.

DETAILED DESCRIPTION OF BEST MODE AND SPECIFIC/PREFERRED EMBODIMENTS OF THE INVENTION

In the context of the present invention, the term "halogen" means chlorine, fluorine, bromine or iodine.

The term "heteroatoms" means nitrogen, oxygen, sulfur or silicon.

The term "aryl" is an aromatic ring, with the exception of phenyl, optionally substituted by one or more $C_1$-$C_4$ alkyl radicals.

The term "$C_3$ to $C_8$ cycloalkyl" is an aliphatic ring having from 3 to 8 carbon atoms, including, for example, cyclopropyl, cyclopentyl and cyclohexyl.

Representative alkyl groups according to the invention include methyl, ethyl, isopropyl, n-propyl, n-butyl, t-butyl, isobutyl, sec-butyl, pentyl, n-hexyl, cyclopropyl, cyclopentyl, cyclohexyl and allyl groups.

According to one embodiment of the invention, a C-glycoside derivative is administered corresponding to the formula (I) for which S can represent a monosaccharide or a polysaccharide containing up to 6 sugar units, in a pyranose and/or furanose form and of the L and/or D series, the said mono- or polysaccharide having at least one necessarily free hydroxyl functional group and/or optionally one or more necessarily protected amine functional groups, X and R furthermore retaining all the definitions given above.

Advantageously, a monosaccharide of the invention can be selected from among D-glucose, D-galactose, D-mannose, D-xylose, D-lyxose, L-fucose, L-arabinose, L-rhamnose, D-glucuronic acid, D-galacturonic acid, D-iduronic acid, N-acetyl-D-glucosamine or N-acetyl-D-galactosamine and advantageously is D-glucose, D-xylose, N-acetyl-D-glucosamine or L-fucose, in particular D-xylose.

More particularly, a polysaccharide of the invention containing up to 6 sugar units can be selected from D-maltose, D-lactose, D-cellobiose, D-maltotriose, a disaccharide combining a uronic acid selected from D-iduronic acid or D-glucuronic acid with a hexosamine selected from D-galactosamine, D-glucosamine, N-acetyl-D-galactosamine or N-acetyl-D-glucosamine, an oligo-saccharide comprising at least one xylose which can advantageously be selected from xylobiose, methyl β-xylobioside, xylotriose, xylotetraose, xylopentaose and xylohexaose, in particular xylobiose, which is composed of two xylose molecules bonded via a 1-4 bond.

More particularly, S can represent a monosaccharide selected from among D-glucose, D-xylose, D-fucose, D-galactose or D-maltose, in particular D-xylose.

According to another embodiment of the invention, C-glycoside derivatives may be administered corresponding to the formula (I) for which X is a group selected from among —CO—, —CH(OH)—, —CH($NR_1R_2$)— or —CH(R)—, in particular —CO—, —CH(OH)—, —C($NH_2$)—, —C($NHCH_2CH_2CH_2OH$)—, —C(NHPh)- or —C($CH_3$)—, and more particularly a —CO—, —CH(OH)— or —CH($NH_2$)— group, preferably a —CH(OH)— group, S and R furthermore retaining all the definitions given above.

According to another embodiment of the invention, a C-glycoside derivative may be administered corresponding to the formula (I) for which R is a saturated linear $C_1$ to $C_{20}$, in particular $C_1$ to $C_{10}$, alkyl radical, an unsaturated linear $C_2$ to $C_{20}$, in particular $C_2$ to $C_{10}$, alkyl radical or a saturated or unsaturated and branched or cyclic $C_3$ to $C_{20}$, in particular $C_3$ to $C_{10}$, alkyl radical, with the exception of the phenyl radical, which is optionally substituted as described above, S and R furthermore retaining all the definitions given above. Preferably, R is a linear $C_1$-$C_4$, in particular $C_1$-$C_3$, radical optionally substituted by —OH, —COOH or —COOR"$_2$, R"$_2$ being a saturated $C_1$-$C_4$ alkyl radical, in particular the ethyl radical. Preferably, R is an unsubstituted linear $C_1$-$C_4$, in particular $C_1$-$C_2$, alkyl radical, in particular the ethyl radical.

Among the C-glycoside derivatives of formula (I), preferred are those in which:

R is a saturated linear $C_1$ to $C_{20}$, in particular $C_1$ to $C_{10}$, alkyl radical, an unsaturated linear $C_2$ to $C_{20}$, in particular $C_2$ to $C_{10}$, alkyl radical or a saturated or unsaturated and branched or cyclic $C_3$ to $C_{20}$, in particular $C_3$ to $C_{10}$, alkyl radical, with the exception of the phenyl radical, which is optionally substituted as described above;

S is a monosaccharide as described above;

X is —CO—, —CH(OH)—, —CH($NR_1R_2$)— or —CH(R)— as described above.

Preferably, a C-glycoside derivative of formula (I) is administered in which:

R is a linear $C_1$-$C_4$, in particular $C_1$-$C_3$, radical optionally substituted by —OH, —COOH or —COOR"$_2$, R"$_2$ being a saturated $C_1$-$C_4$ alkyl radical, in particular the ethyl radical;

S is a monosaccharide as described above;

X is a group selected from —CO—, —CH(OH)—, —C(NH$_2$)—, —C(NHCH$_2$CH$_2$CH$_2$OH)—, —C(NHPh)- or —C(CH$_3$)—, more particularly a —CO—, —CH(OH)— or —CH(NH$_2$)— group and preferably a —CH(OH)— group.

Preferably, a C-glycoside derivative of formula (I) is administered in which:

R is an unsubstituted linear C$_1$-C$_4$, in particular C$_1$-C$_2$, alkyl radical, in particular the ethyl radical;

S is a monosaccharide as described above, in particular D-glucose, D-xylose, N-acetyl-D-glucosamine or L-fucose and especially D-xylose;

X is a group selected from —CO—, —CH(OH)— or —CH(NH$_2$)— and preferably a —CH(OH)— group.

The salts acceptable for the non-therapeutic administration of the compounds of the present invention comprise conventional non-toxic salts of the said compounds, such as those formed from organic or inorganic acids. Representative are the salts of inorganic acids, such as sulfuric acid, hydrochloric acid, hydrobromic acid, hydriodic acid, phosphoric acid or boric acid. Also representative are the salts of organic acids which can comprise one or more carboxylic, sulfonic or phosphonic acid groups. They can be linear, branched or cyclic aliphatic acids or also aromatic acids. These acids can additionally comprise one or more heteroatoms selected from O and N, for example in the form of hydroxyl groups. Particularly representative are propionic acid, acetic acid, terephthalic acid, citric acid and tartaric acid.

When the compound of formula (I) comprises an acid group, the neutralization of the acid group or groups can be carried out with an inorganic base, such as LiOH, NaOH, KOH, Ca(OH)$_2$, NH$_4$OH, Mg(OH)$_2$ or Zn(OH)$_2$, or with an organic base, such as a primary, secondary or tertiary alkylamine, for example triethylamine or butylamine. This primary, secondary or tertiary alkylamine can comprise one or more nitrogen and/or oxygen atoms and can thus comprise, for example, one or more alcohol functional groups; representative are 2-amino-2-methylpropanol, triethanolamine, 2-(dimethylamino)propanol or 2-amino-2-(hydroxymethyl)-1,3-propanediol. Also representative are lysine or 3-(dimethylamino)propylamine.

The solvates acceptable for the compounds of the present invention comprise conventional solvates, such as those formed during the final stage of preparation of the said compounds due to the presence of solvents. Representative are the solvates due to the presence of water or of linear or branched alcohols, such as ethanol or isopropanol.

Particularly preferred C-glycoside compounds of formula (I) according to the invention are:
1. C-β-D-xylopyranoside-n-propan-2-one;
2. C-α-D-xylopyranoside-n-propan-2-one;
3. 1-[2-(3-hydroxypropylamino)propyl]-C-β-D-xylopyranose;
4. 1-[2-(3-hydroxypropylamino)propyl]-C-α-D-xylopyranose;
5. C-β-D-xylopyranoside-2-hydroxypropane;
6. C-α-D-xylopyranoside-2-hydroxypropane;
7. C-β-D-xylopyranoside-2-aminopropane;
8. C-α-D-xylopyranoside-2-aminopropane;
9. C-β-D-xylopyranoside-2-(phenylamino)propane;
10. C-α-D-xylopyranoside-2-(phenylamino)propane;
11. ethyl ester of 3-methyl-4-(C-β-D-xylopyranoside)butyric acid;
12. ethyl ester of 3-methyl-4-(C-α-D-xylopyranoside)butyric acid;
13. 6-(C-β-D-xylopyranoside)-5-ketohexanoic acid;
14. 6-(C-α-D-xylopyranoside)-5-ketohexanoic acid;
15. 6-(C-β-D-xylopyranoside)-5-hydroxyhexanoic acid;
16. 6-(C-α-D-xylopyranoside)-5-hydroxyhexanoic acid;
17. 6-(C-β-D-xylopyranoside)-5-aminohexanoic acid;
18. 6-(C-α-D-xylopyranoside)-5-aminohexanoic acid;
19. 6-(C-β-D-xylopyranoside)-5-(phenylamino)hexanoic acid;
20. 6-(C-α-D-xylopyranoside)-5-(phenylamino)hexanoic acid;
21. 1-(C-β-D-xylopyranoside)hexane-2,6-diol;
22. 1-(C-α-D-xylopyranoside)hexane-2,6-diol;
23. 5-(C-β-D-xylopyranoside)-4-ketopentanoic acid;
24. 5-(C-α-D-xylopyranoside)-4-ketopentanoic acid;
25. 5-(C-β-D-xylopyranoside)-4-hydroxypentanoic acid;
26. 5-(C-α-D-xylopyranoside)-4-hydroxypentanoic acid;
27. 5-(C-β-D-xylopyranoside)-4-aminopentanoic acid;
28. 5-(C-α-D-xylopyranoside)-4-aminopentanoic acid;
29. 5-(C-β-D-xylopyranoside)-4-(phenylamino)pentanoic acid;
30. 5-(C-α-D-xylopyranoside)-4-(phenylamino)pentanoic acid;
31. 1-(C-β-D-xylopyranoside)pentane-2,5-diol;
32. 1-(C-α-D-xylopyranoside)pentane-2,5-diol;
33. 1-(C-β-D-fucopyranoside)propan-2-one;
34. 1-(C-α-D-fucopyranoside)propan-2-one;
35. 1-(C-β-L-fucopyranoside)propan-2-one;
36. 1-(C-α-L-fucopyranoside)propan-2-one;
37. 1-(C-β-D-fucopyranoside)-2-hydroxypropane;
38. 1-(C-α-D-fucopyranoside)-2-hydroxypropane;
39. 1-(C-β-L-fucopyranoside)-2-hydroxypropane;
40. 1-(C-α-L-fucopyranoside)-2-hydroxypropane;
41. 1-(C-β-D-fucopyranoside)-2-aminopropane;
42. 1-(C-α-D-fucopyranoside)-2-aminopropane;
43. 1-(C-β-L-fucopyranoside)-2-aminopropane;
44. 1-(C-α-L-fucopyranoside)-2-aminopropane;
45. 1-(C-β-D-fucopyranoside)-2-(phenylamino)propane;
46. 1-(C-α-L-fucopyranoside)-2-(phenylamino)propane;
47. 1-(C-β-L-fucopyranoside)-2-(phenylamino)propane;
48. 1-(C-α-L-fucopyranoside)-2-(phenylamino)propane;
49. ethyl ester of 3-methyl-4-(C-β-D-fucopyranoside)butyric acid;
50. ethyl ester of 3-methyl-4-(C-α-L-fucopyranoside)butyric acid;
51. ethyl ester of 3-methyl-4-(C-β-L-fucopyranoside)butyric acid;
52. ethyl ester of 3-methyl-4-(C-α-L-fucopyranoside)butyric acid;
53. 6-(C-β-D-fucopyranoside)-5-ketohexanoic acid;
54. 6-(C-α-D-fucopyranoside)-5-ketohexanoic acid;
55. 6-(C-β-L-fucopyranoside)-5-ketohexanoic acid;
56. 6-(C-α-L-fucopyranoside)-5-ketohexanoic acid;
57. 6-(C-β-D-fucopyranoside)-5-hydroxyhexanoic acid;
58. 6-(C-α-D-fucopyranoside)-5-hydroxyhexanoic acid;
59. 6-(C-β-L-fucopyranoside)-5-hydroxyhexanoic acid;
60. 6-(C-α-L-fucopyranoside)-5-hydroxyhexanoic acid;
61. 6-(C-β-D-fucopyranoside)-5-aminohexanoic acid;
62. 6-(C-α-L-fucopyranoside)-5-aminohexanoic acid;
63. 6-(C-β-L-fucopyranoside)-5-aminohexanoic acid;
64. 6-(C-α-L-fucopyranoside)-5-aminohexanoic acid;
65. 1-(C-β-D-fucopyranoside)hexane-2,6-diol;
66. 1-(C-α-D-fucopyranoside)hexane-2,6-diol;
67. 1-(C-β-L-fucopyranoside)hexane-2,6-diol;
68. 1-(C-α-L-fucopyranoside)hexane-2,6-diol;
69. 5-(C-β-D-fucopyranoside)-4-ketopentanoic acid;
70. 5-(C-α-D-fucopyranoside)-4-ketopentanoic acid;
71. 5-(C-β-L-fucopyranoside)hexane-2,6-diol)-4-ketopentanoic acid;

72. 5-(C-α-L-fucopyranoside)hexane-2,6-diol)-4-ketopentanoic acid;
73. 5-(C-β-D-fucopyranoside)-4-hydroxypentanoic acid;
74. 5-(C-α-D-fucopyranoside)-4-hydroxypentanoic acid;
75. 5-(C-β-L-fucopyranoside)-4-hydroxypentanoic acid;
76. 5-(C-α-L-fucopyranoside)-4-hydroxypentanoic acid;
77. 5-(C-β-D-fucopyranoside)-4-aminopentanoic acid;
78. 5-(C-α-D-fucopyranoside)-4-aminopentanoic acid;
79. 5-(C-β-L-fucopyranoside)-4-aminopentanoic acid;
80. 5-(C-α-L-fucopyranoside)-4-aminopentanoic acid;
81. 1-(C-β-D-fucopyranoside)pentane-2,5-diol;
82. 1-(C-α-D-fucopyranoside)pentane-2,5-diol;
83. 1-(C-β-L-fucopyranoside)pentane-2,5-diol;
84. 1-(C-α-L-fucopyranoside)pentane-2,5-diol;
85. 1-(C-β-D-glucopyranosyl)-2-hydroxypropane;
86. 1-(C-α-D-glucopyranosyl)-2-hydroxypropane;
87. 1-(C-β-D-glucopyranosyl)-2-aminopropane;
88. 1-(C-α-D-glucopyranosyl)-2-aminopropane;
89. 1-(C-β-D-glucopyranosyl)-2-(phenylamino)propane;
90. 1-(C-α-D-glucopyranosyl)-2-(phenylamino)propane;
91. ethyl ester of 3-methyl-4-(C-β-D-glucopyranosyl)butyric acid;
92. ethyl ester of 3-methyl-4-(C-α-D-glucopyranosyl)butyric acid;
93. 6-(C-β-D-glucopyranosyl)-5-ketohexanoic acid;
94. 6-(C-α-D-glucopyranosyl)-5-ketohexanoic acid;
95. 6-(C-β-D-glucopyranosyl)-5-hydroxyhexanoic acid;
96. 6-(C-α-D-glucopyranosyl)-5-hydroxyhexanoic acid;
97. 6-(C-β-D-glucopyranosyl)-5-aminohexanoic acid;
98. 6-(C-α-D-glucopyranosyl)-5-aminohexanoic acid;
99. 6-(C-β-D-glucopyranosyl)-5-(phenylamino)hexanoic acid;
100. 6-(C-α-D-glucopyranosyl)-5-(phenylamino)hexanoic acid;
101. 1-(C-β-D-glucopyranosyl)hexane-2,6-diol;
102. 1-(C-α-D-glucopyranosyl)hexane-2,6-diol;
103. 6-(C-β-D-glucopyranosyl)-5-ketopentanoic acid;
104. 6-(C-α-D-glucopyranosyl)-5-ketopentanoic acid;
105. 6-(C-β-D-glucopyranosyl)-5-hydroxypentanoic acid;
106. 6-(C-α-D-glucopyranosyl)-5-hydroxypentanoic acid;
107. 6-(C-β-D-glucopyranosyl)-5-aminopentanoic acid;
108. 6-(C-α-D-glucopyranosyl)-5-aminopentanoic acid;
109. 6-(C-β-D-glucopyranosyl)-5-(phenylamino)pentanoic acid;
110. 6-(C-α-D-glucopyranosyl)-5-(phenylamino)pentanoic acid;
111. 1-(C-β-D-glucopyranosyl)pentane-2,5-diol;
112. 1-(C-α-D-glucopyranosyl)pentane-2,5-diol;
113. 1-(C-β-D-galactopyranosyl)-2-hydroxypropane;
114. 1-(C-α-D-galactopyranosyl)-2-hydroxypropane;
115. 1-(C-β-D-galactopyranosyl)-2-aminopropane;
116. 1-(C-α-D-galactopyranosyl)-2-aminopropane;
117. 1-(C-β-D-galactopyranosyl)-2-(phenylamino)propane;
118. 1-(C-α-D-galactopyranosyl)-2-(phenylamino)propane;
119. ethyl ester of 3-methyl-4-(C-β-D-galactopyranosyl)butyric acid;
120. ethyl ester of 3-methyl-4-(C-α-D-galactopyranosyl)butyric acid;
121. 6-(C-β-D-galactopyranosyl)-5-ketohexanoic acid;
122. 6-(C-α-D-galactopyranosyl)-5-ketohexanoic acid;
123. 6-(C-β-D-galactopyranosyl)-5-hydroxyhexanoic acid;
124. 6-(C-α-D-galactopyranosyl)-5-hydroxyhexanoic acid;
125. 6-(C-β-D-galactopyranosyl)-5-aminohexanoic acid;
126. 6-(C-α-D-galactopyranosyl)-5-aminohexanoic acid;
127. 6-(C-β-D-galactopyranosyl)-5-(phenylamino)hexanoic acid;
128. 6-(C-α-D-galactopyranosyl)-5-(phenylamino)hexanoic acid;
129. 1-(C-β-D-galactopyranosyl)hexane-2,6-diol;
130. 1-(C-α-D-galactopyranosyl)hexane-2,6-diol;
131. 6-(C-β-D-galactopyranosyl)-5-ketopentanoic acid;
132. 6-(C-α-D-galactopyranosyl)-5-ketopentanoic acid;
133. 6-(C-β-D-galactopyranosyl)-5-hydroxypentanoic acid;
134. 6-(C-α-D-galactopyranosyl)-5-hydroxypentanoic acid;
135. 6-(C-β-D-galactopyranosyl)-5-aminopentanoic acid;
136. 6-(C-α-D-galactopyranosyl)-5-aminopentanoic acid;
137. 6-(C-β-D-galactopyranosyl)-5-(phenylamino)pentanoic acid;
138. 6-(C-α-D-galactopyranosyl)-5-(phenylamino)-pentanoic acid;
139. 1-(C-β-D-galactopyranosyl)pentane-2,6-diol;
140. 1-(C-α-D-galactopyranosyl)pentane-2,6-diol;
141. 1-(C-β-D-fucofuranosyl)propan-2-one;
142. 1-(C-α-D-fucofuranosyl)propan-2-one;
143. 1-(C-β-L-fucofuranosyl)propan-2-one;
144. 1-(C-α-L-fucofuranosyl)propan-2-one;
145. 3'-(acetamido-C-β-D-glucopyranosyl)propan-2'-one;
146. 3'-(acetamido-C-α-D-glucopyranosyl)propan-2'-one;
147. 1-(C-β-D-galactopyranosyl)-2-hydroxypropane;
148. 1-(C-α-D-galactopyranosyl)-2-aminopropane;
149. 1-(acetamido-C-β-D-glucopyranosyl)-2-(phenylamino)propane;
150. 1-(acetamido-C-α-D-glucopyranosyl)-2-(phenylamino)propane;
151. ethyl ester of 3-methyl-4-(acetamido-C-β-D-glucopyranosyl)butyric acid;
152. ethyl ester of 3-methyl-4-(acetamido-C-α-D-glucopyranosyl)butyric acid;
153. 6-(acetamido-C-β-D-glucopyranosyl)-5-ketohexanoic acid;
154. 6-(acetamido-C-α-D-glucopyranosyl)-5-ketohexanoic acid;
155. 6-(acetamido-C-β-D-glucopyranosyl)-5-hydroxyhexanoic acid;
156. 6-(acetamido-C-α-D-glucopyranosyl)-5-hydroxy-hexanoic acid;
157. 6-(acetamido-C-β-D-glucopyranosyl)-5-aminohexanoic acid;
158. 6-(acetamido-C-α-D-glucopyranosyl)-5-aminohexanoic acid;
159. 6-(acetamido-C-β-D-glucopyranosyl)-5-(phenylamino)hexanoic acid;
160. 6-(acetamido-C-α-D-glucopyranosyl)-5-(phenylamino)-hexanoic acid;
161. 1-(acetamido-C-β-D-glucopyranosyl)hexane-2,6-diol;
162. 1-(acetamido-C-α-D-glucopyranosyl)hexane-2,6-diol;
163. 6-(acetamido-C-β-D-glucopyranosyl)-5-ketopentanoic acid;
164. 6-(acetamido-C-α-D-glucopyranosyl)-5-ketopentanoic acid;
165. 6-(acetamido-C-β-D-glucopyranosyl)-5-hydroxypentanoic acid;
166. 6-(acetamido-C-α-D-glucopyranosyl)-5-hydroxy-pentanoic acid;
167. 6-(acetamido-C-β-D-glucopyranosyl)-5-aminopentanoic acid;
168. 6-(acetamido-C-α-D-glucopyranosyl)-5-aminopentanoic acid;
169. 6-(acetamido-C-β-D-glucopyranosyl)-5-(phenylamino)pentanoic acid;
170. 6-(acetamido-C-α-D-glucopyranosyl)-5-(phenylamino)pentanoic acid;

171. 1-(acetamido-C-β-D-glucopyranosyl)pentane-2,5-diol;
172. 1-(acetamido-C-α-D-glucopyranosyl)pentane-2,5-diol.

Among these, preferred are C-α-D-xylopyranoside-2-hydroxypropane and C-β-D-xylopyranoside-2-hydroxypropane, notably C-β-D-xylopyranoside-2-hydroxypropane.

Of course, according to the invention, the C-glycoside derivatives corresponding to the formula (I) can be used alone or as a mixture and in any proportion.

According to the invention, the C-glycoside derivatives corresponding to the formula (I) can be of natural or synthetic origin, completely or partly purified or any preparation comprising same.

The term "natural origin" means a derivative extracted from natural material in which it is present, for example, plants. The term "synthetic origin" means a derivative prepared by chemical synthesis or by biotechnology.

The expression "completely or partially purified" means here that, during its synthesis or in comparison with its natural state (fresh or dried plant or cells), the C-glycoside derivative corresponding to the formula (I) in the composition of the invention has been concentrated and/or has been freed respectively from at least a portion of the reaction by-products resulting from its synthesis or from at least a portion of the other constituents of the natural material in which it is present.

The C-glycoside derivatives can in particular be prepared by the synthetic method disclosed in EP-1-345,919.

The compounds of formula (I) according to the invention are useful to effectively depigment and/or lighten human skin.

The pigmenting of the skin is a normal physiological process resulting from the exposure of the skin to sunlight.

It may, for the purpose of attractiveness, be desirable to render the appearance of the skin more beautiful by limiting pigmentation and thus to reduce the onset of darker skin regions.

It also transpires that the pigmentation results from skin disorders which can, for example, be related to a local proliferation of active melanocytes.

The C-glycosides are in particular applied to the skin of individuals exhibiting brownish pigmentation blemishes or blemishes due to aging or to the skin of individuals wishing to combat the onset of a brownish color resulting from melanogenesis, for example following exposure to ultraviolet radiation.

Thus, the compounds of formula (I) are useful as whitening agents for the skin and/or as anti-browning agents, in particular for preventing the formation of and/or softening pigment blemishes, freckles or blemishes due to aging and/or for lightening and/or whitening and/or rendering uniform the color of browned skin.

These compounds are particularly effective in preventing and/or treating sun spots. Sun spots, also known as senile lentigines, are characterized by small brown maculae corresponding to greater local production of melanin induced by chronic exposure to the sun. They are generally encountered on the face, backs of the hands, forearms, top of the back and of the neckline, and even the scalp regions of the scalp devoid of hair.

The present invention consequently features the use of a compound of formula (I) as defined above in the manufacture of a dermatological composition useful to treat pigment disorders of the skin.

The compounds of formula (I) may also be of use in treating regional hyperpigmentations by melanocytic hyperactivity, such as melasma of the forearms, idiopathic melasmas, arising during pregnancy ("mask of pregnancy" or chloasma) or oestrone/progestogen contraception, PUVA lentigines, post-inflammatory hyperpigmentation, accidental hyperpigmentations, possibly due to photosensitization or to post-lesional healing, as well as certain leucodermas, such as vitiligo.

The depigmenting substances also have an application in the whitening of the superficial body growths, in particular of the body hairs, which it may be desirable to lighten in order to render them less visible.

Whether the compounds of formula (I) are used for cosmetic or pharmaceutical purposes, they can be administered by various routes, for example the oral route. These compounds will then be formulated in compositions appropriate for this method of administration.

For ingestion, numerous embodiments of oral compositions and in particular of food additives are possible. They are formulated by conventional processes for producing tablets, including sugar-coated tablets, capsules, hard gelatin capsules, gels or emulsions. In particular, the active principle(s) according to the invention can be incorporated in any other form of food supplements or enriched foods, for example food bars, or compacted or non-compacted powders. The powders can be diluted in water, fizzy drinks, dairy products or soya derivatives or can be incorporated in food bars.

This invention thus also features a cosmetic regime or regimen for whitening human skin and/or whitening the scalp and/or whitening mucous membranes, comprising the ingestion or the topical application to the skin and/or scalp and/or mucous membranes of at least one C-glycoside compound.

In the case of a topical application, the C-glycoside compound can be maintained in contact with the skin and/or scalp and/or mucous membranes and can then optionally be rinsed off.

The process is suitable in particular for removing brownish pigment blemishes and/or blemishes due to aging and/or for lightening browned skin.

With a view to their topical application, the compounds of formula (I) can be formulated in a composition comprising a physiologically acceptable medium.

In particular, the composition is suitable for topical application to the skin. The physiologically acceptable medium will preferably be a cosmetically or dermatologically acceptable medium, that is to say without an unpleasant appearance and which does not cause smarting, tightness or redness unacceptable to the user.

The term "physiologically acceptable medium" means a medium compatible with human keratinous substances, such as the skin, mucous membranes, nails, scalp and/or hair.

The compositions according to the invention are useful for a cosmetic or pharmaceutical, particularly dermatological, application.

The amount of compounds of formula (I) which can be administered according to the invention depends very obviously on the effect desired.

By way of example and for administration by the topical route, this amount can range, for example, from 0.0001% to 25% by weight, 0.001% to 10% by weight, preferably from 0.01% to 5% by weight, in particular from 0.1% to 2% by weight, with respect to the total weight of the composition.

In the case of administration by the oral route, the amount of compound of formula (I) can be from 10 and 1000 mg weight/kg of body weight/day, preferably 100 mg weight/kg of body weight/day.

In the case or oral administration, the composition can be provided in the form of tablets, including sugar-coated tablets, hard gelatin capsules, syrups, suspensions, solutions, powders, granules, emulsions, suspensions of microspheres or nanospheres or vesicles of lipid or polymer type making possible controlled release. Preferably, the composition is provided in the supplement form.

In the case of topical administration, the composition can comprise the constituents conventionally employed in the application envisaged.

Particularly representative are water, solvents, oils of mineral, animal and/or vegetable origin, waxes, pigments, fillers, surfactants, cosmetic or dermatological active principles, UV screening agents, polymers, gelling agents or preservatives.

Of course, one skilled in the art will take care to choose this or these optional additional compounds and/or their amounts so that the advantageous properties of the compounds according to the invention are not, or not substantially, detrimentally affected by the envisaged addition.

The compositions according to the invention can be provided in any formulation form normally employed in the cosmetic and dermatological fields; it can in particular be in the form of an aqueous or aqueous/alcoholic solution which is optionally gelled, of a dispersion of the optionally two-phase lotion type, of an oil-in-water or water-in-oil or multiple emulsion, of an aqueous gel, of a dispersion of oil in an aqueous phase using spherules, it being possible for these spherules to be polymer nanoparticles, such as nanospheres and nanocapsules, or lipid vesicles of ionic and/or non-ionic type.

When the composition of the invention is an emulsion, the proportion of the fatty phase can range from 5% to 80% by weight and preferably from 5% to 50% by weight, with respect to the total weight of the composition. The oils, the emulsifiers and the optional coemulsifiers used in the composition in the emulsion form are selected from those conventionally employed in the field under consideration. The emulsifying agent and the coemulsifying agent are present in the composition in a proportion ranging from 0.3% to 30% by weight and preferably from 0.5% to 20% by weight, with respect to the total weight of the composition.

This composition can be more or less fluid and have the appearance of a white or colored cream, of an ointment, of a milk, or a lotion, of a serum, of a paste or of a foam. It can optionally be applied to the skin in the aerosol form. It can optionally be provided in the solid form, for example in the stick form. It can be used as care product and/or as makeup product.

This composition can constitute a cleansing, protective, treatment or care cream for the face, for the hands, for the feet, for the major anatomical folds or for the body (for example, day creams, night creams, make-up-removing creams, foundation creams or sunscreens), a liquid foundation, a make-up-removing milk, a protective or care body milk, a sun milk or a lotion, gel or foam for caring for the skin, such as a cleansing lotion.

In an advantageous embodiment of the invention, the compositions can additionally comprise at least one depigmenting agent and/or one desquamating agent and/or at least one soothing agent and/or at least one organic photoprotective agent and/or at least one inorganic photoprotective agent.

Including at least one C-glycoside compound in combination with another depigmenting agent can make it possible in particular to use a lower amount of each of the depigmenting agents.

The term "depigmenting" agent means, for example, depigmenting or anti-pigmenting agents such as the following compounds: kojic acid; ellagic acid; arbutin and its derivatives, such as those disclosed in EP-895,779 and EP-524,109; hydroquinone; aminophenol derivatives, such as those disclosed in WO 99/10318 and WO 99/32077, in particular N-cholesteryloxycarbonyl-para-aminophenol and N-ethyloxycarbonyl-para-aminophenol; iminophenol derivatives, in particular those disclosed in WO 99/22707; L-2-oxothiazolidine-4-carboxylic acid or procysteine, and its salts and esters; calcium D-pantetheinesulfonate; ascorbic acid and its derivatives, in particular ascorbyl glucoside; and plant extracts, in particular of liquorice, of blackberry, of skull cap and of *Bacopa monnieri*, without this list being limiting.

In particular, the C-glycoside can be combined in a composition with ascorbic acid (vitamin C) and/or one of its analogues or derivatives.

The analogues or derivatives of ascorbic acid are more particularly its salts, such as in particular sodium ascorbate, magnesium ascorbyl phosphate or sodium ascorbyl phosphate, its esters, such as in particular its acetic, propionic or palmitic esters, or its sugars, such as in particular glycosylated ascorbic acid.

Due to its chemical structure ($\alpha$-ketolactone), which renders it highly sensitive to certain environmental parameters, such as light, heat and aqueous media, it can be advantageous to use ascorbic acid in the form of a monosaccharide ester of ascorbic acid or of a metal salt of phosphorylated ascorbic acid.

The monosaccharide esters of ascorbic acid which can be used in the invention are in particular the glucose, mannose, fructose, fucose, galactose, N-acetylglucosamine or N-acetylmuramic derivatives of ascorbic acid and their mixtures and more especially 2-ascorbyl glucoside or 2-O-($\alpha$-D-glucopyranosyl)-L-ascorbic acid or also 6-O-($\beta$-D-galactopyranosyl)-L-ascorbic acid. The latter compounds and their preparation processes are disclosed in particular in the EP-A487,404, EP-A425,066 and J05213736.

For its part, the metal salt of phosphorylated ascorbic acid is selected from alkali metal ascorbyl phosphates, alkaline earth metal ascorbyl phosphates and transition metal ascorbyl phosphates. Use is advantageously made of magnesium ascorbyl phosphate.

The term "desquamating agent" means any compound capable of acting:
  either directly on desquamation by promoting exfoliation, such as $\beta$-hydroxy acids, in particular salicylic acid and its derivatives (including 5-(n-octanoyl)salicylic acid); $\alpha$-hydroxy acids, such as glycolic acid, citric acid, lactic acid, tartaric acid, malic acid or mandelic acid; urea; gentisic acid; oligofucoses; cinnamic acid; *Saphora japonica* extract; resveratrol;
  or on the enzymes involved in desquamation or decomposition of the corneodesmosomes, such as glycosidases, stratum corneum chymotryptic enzyme (SCCE) or indeed even other proteases (trypsin, chymotrypsin-like). Representative are agents which chelate inorganic salts: EDTA; N-acyl-N,N',N'-ethylenediaminetriacetic acid; aminosulfonic compounds and in particular N-(2-hydroxyethyl) piperazine-N'-2-ethanesulfonic acid (HEPES); 2-oxothiazolidine-4-carboxylic acid (procysteine) derivatives; derivatives of $\alpha$-amino acids of glycine type (as disclosed in EP-0 852 949, and also the sodium methylglycinediacetate marketed by BASF under the trade name TRILON M™); honey; or sugar derivatives, such as O-octanoyl-6-D-maltose and N-acetylglucosamine.

Representative soothing agents which can be included in the compositions according to the invention are pentacyclic triterpenes and plant extracts (for example, *Glycyrrhiza glabra*) comprising them, such as $\beta$-glycyrrhetinic acid and its salts and/or its derivatives (glycyrrhetinic acid monoglucuronide, stearyl glycyrrhetinate or 3-stearoyloxyglycyrrhetic acid), ursolic acid and its salts, oleanolic acid and its salts, betulinic acid and its salts, an extract of *Paeonia suffruticosa* and/or *lactiflora*, salts of salicylic acid and in particular zinc salicylate, phycosaccharides from Codif, an extract of *Laminaria saccharina*, canola oil, bisabolol, camomile extracts, allantoin, SEPIVITAL EPC™ (phosphoric diester of vitamin E and C) from Seppic, omega-3 unsaturated oils, such as musk rose, blackcurrant seed, echium or fish oils, plankton extracts, capryloylglycine, SEPPICALM VG™ (sodium palmitoylproline and *Nymphaea alba*) from Seppic, an extract of *Pygeum*, an extract of *Boswellia serrata*, an extract of *Centipeda cunninghami*, an extract of *Helianthus annuus*, an extract of *Linum usitatissimum*, tocotrienols, extracts of *Cola nitida*, piperonal, an extract of clove, an extract of *Epilobium angustifolium, aloe vera*, an extract of *Bacopa monnieri*, phytosterols, cortisone, hydrocortisone, indomethacin and betamethasone.

The organic photoprotective agents are selected in particular from among anthranilates; cinnamic derivatives; dibenzoylmethane derivatives; salicylic derivatives; camphor derivatives; triazine derivatives, such as those disclosed in U.S. Pat. No. 4,367,390, EP 0 863 145, EP 0 517 104, EP 0 570 838, EP 0 796 851, EP0 775698, EP0 878469, EP0 933376, EP0 507691, EP0 507 692, EP 0 790 243 and EP 0 944 624; benzophenone derivatives; β,β-diphenylacrylate derivatives; benzotriazole derivatives; benzalmalonate derivatives; benzimidazole derivatives; imidazolines; bis-benzoazolyl derivatives, such as disclosed in EP-0-669,323 and U.S. Pat. No. 2,463,264; p-aminobenzoic acid (PABA) derivatives; methylenebis(hydroxyphenyl benzotriazole) derivatives, such as disclosed in U.S. Pat. Nos. 5,237,071, 5,166,355, GB-2,303,549, DE-197,26,184 and EP-0-893, 119; and screening polymers and screening silicones, such as those disclosed in particular in WO 93/04665; dimers derived from α-alkylstyrene, such as those disclosed in DE-198,55, 649.

The inorganic photoprotective agents are selected from among pigments or, alternatively, nanopigments (mean size of the primary particles: generally from 5 nm and 100 nm, preferably from 10 nm and 50 nm) formed of coated or non-coated metal oxides, such as, for example, titanium oxide (amorphous or crystalline in the rutile and/or anatase form), iron oxide, zinc oxide, zirconium oxide or cerium oxide nanopigments, which are all UV protective agents well known per se. Conventional coating agents are furthermore alumina and/or aluminum stearate. Such nanopigments, formed of coated or non-coated metal oxides, are disclosed in particular in EP-0-518,772 and EP-0-518,773.

The photoprotective agents are generally present in the compositions according to the invention in proportions ranging from 0.1% to 20% by weight, with respect to the total weight of the composition, and preferably ranging from 0.2% to 15% by weight, with respect to the total weight of the composition.

Preferably, the C-glycoside derivative or derivatives will be administered in combination with at least one depigmenting agent and/or at least one photoprotective agent.

In order to further illustrate the present invention and the advantages thereof, the following specific examples are given, it being understood that same are intended only as illustrative and in nowise limitative. In said examples to follow, all parts and percentages are given by weight, unless otherwise indicated.

Also in said examples to follow, the compounds are, as the case may be, indicated under their chemical names or under their CTFA (International Cosmetic Ingredient Dictionary and Handbook) names.

EXAMPLE 1

Demonstration of the depigmenting activity of C-β-D-xylopyranoside-2-hydroxypropane:

A double blind comparative single-center clinical study (active principle versus placebo composed of the vehicle of the active principle, see the formulation described in detail below) randomized with regard to its location (the subject being her own control) was carried out on 15 women with an average age of 62 years, of phototype III (on a scale with 6 levels: I—always burns, never tans; II—always burns, tans slightly; III—burns moderately, tans progressively; IV—burns minimally, tans very easily; V—burns rarely, tans profusely; VI—never burns, highly pigmented), exhibiting moderate signs of overall aging of the face.

A clinical evaluation of actinic lentigines was carried out by a dermatologist at the beginning and at the end of the study according to a scale with 7 levels, including 4 main levels:
 0—absent;
 1—few blemishes;
 2—many blemishes;
 3—a great many blemishes;
and 3 intermediate levels (0.5; 1.5; 2.5).

The women applied C-β-D-xylopyranoside-2-hydroxypropane at a concentration of 10% by weight with respect to the total weight of the composition in a proportion of 2 mg/cm$^2$ or the placebo twice daily for 3 months (98 days) to the pre-marked regions.

Composition of the Excipient:

| Chemical Name | |
|---|---|
| WHITE PETROLATUM | 4 |
| SORBITAN TRISTEARATE | 0.9 |
| POLYETHYLENE GLYCOL (40 EO) STEARATE | 2 |
| FRAGRANCE | 0.25 |
| MYRISTYL MYRISTATE | 2 |
| MIXTURE OF METHYL, BUTYL, ETHYL, PROPYL AND ISOBUTYL (7/57/22/14) p-HYDROXYBENZOATES | 0.3 |
| GLYCERYL MONO/DISTEARATE (36/64)/POTASSIUM STEARATE MIXTURE | 3 |
| HYDROGENATED ISOPARAFFIN (6-8 MOL OF ISOBUTYLENE) | 8.5 |
| PURE SODIUM HYDROXIDE | 0.05 |
| GLYCEROL | 3 |
| MICROBIOLOGICALLY CLEAN DEIONIZED WATER | 35.84 |
| CHLORHEXIDINE DIGLUCONATE IN SOLUTION | 0.25 |
| CYCLOPENTADIMETHYLSILOXANE | 5 |
| PURE DOUBLY-DISTILLED CETYL ALCOHOL | 4 |
| FATTY ACID (PREDOMINANTLY STEARIC ACID) OF VEGETABLE ORIGIN | 1.2 |
| ETHYLENEDIAMINETETRAACETIC ACID, DISODIUM SALT, 2H$_2$O | 0.15 |
| DL-α-TOCOPHERYL ACETATE (VITAMIN E ACETATE) | 0.3 |
| PROTECTED 2-ETHYLHEXYL 4-METHOXYCINNAMATE | 0.52 |
| 1,5-ANHYDRO-6,8-DIDEOXY-L-GLUCO-OCTITOL AT 30% IN WATER | 28.74 |

The mean score on the side treated with C-β-D-xylopyranoside-2-hydroxypropane decreases from 1.07+/−0.62 before treatment to 0.93+/−0.68 (p=0.08), whereas, on the placebo side, this score increases from 1.10+/−0.69 to 1.13 +/−0.67 (NS).

Thus, 54% of the subjects exhibit a lower score on the treated side versus 13% at the beginning of the study.

EXAMPLE 2

Example of a Topical Composition

A whitening cream for caring for the face of oil-in-water emulsion type is prepared comprising (% by weight):

| | |
|---|---|
| C-β-D-Xylopyranoside-2-hydroxy-propane | 0.005% |
| Glyceryl stearate | 2% |
| Polysorbate 60 (Tween 60 from ICI) | 1% |
| Stearic acid | 1.4% |
| Triethanolamine | 0.7% |
| Carbomer | 0.4% |
| Liquid fraction of shea butter | 12% |
| Perhydrosqualene | 12% |
| Antioxidant | 0.05% |
| Fragrance, preservative | q.s. |
| Water | q.s. for 100% |

EXAMPLE 3

Example of a Topical Composition

A depigmenting gel for the skin is prepared comprising (% by weight):

| | |
|---|---|
| C-β-D-Xylopyranoside-2-hydroxy-propane | 2% |
| Hydroxypropylcellulose (Klucel H from Hercules) | 1% |
| Antioxidant | 0.05% |
| Isopropanol | 40% |
| Fragrance, preservative | q.s. |
| Water | q.s. for 100% |

EXAMPLE 4

Example of an Oral Composition

Sugar-Coated Tablets are Prepared Comprising (% by Weight):
Active Materials Mg/Sugar-Coated Tablet:

| | |
|---|---|
| C-β-D-Xylopyranoside-2-hydroxy-propane | 300 |

Excipient of the Core of the Sugar-Coated Tablet:

| | |
|---|---|
| Microcrystalline cellulose | 70 |
| Encompress ™ | 60 |
| Magnesium stearate | 3 |
| Anhydrous colloidal silica | 1 |

Coating Agent:

| | |
|---|---|
| Lac | 5 |
| Talc | 61 |
| Polyvidone | 6 |

This type of sugar-coated tablet can be taken 1 to 4 times daily.

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for depigmenting/whitening the skin and/or for the anti-browning thereof, comprising topically administering to an area of hyperpigmentation on an individual in need of such treatment, for such period of time as required to elicit the desired response of depigmenting/whitening the skin and/or for the anti-browning thereof, a thus effective amount of at least one C-glycoside compound having the following formula (I):

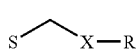

(I)

in which:

R is:

a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;

a saturated linear $C_1$ to $C_{20}$ hydrofluoro- or perfluoroalkyl radical, an unsaturated linear $C_2$ to $C_{20}$ hydrofluoro- or perfluoroalkyl radical or a saturated or unsaturated and branched or cyclic $C_3$ to $C_{20}$, hydrofluoro- or perfluoroalkyl radical;

with the proviso that the hydrocarbon chain constituting said radicals may be interrupted by 1, 2, 3 or more heteroatoms selected from the group consisting of:

an oxygen atom, a sulfur atom, a nitrogen atom, and a silicon atom, and with the further proviso that the hydrocarbon chain constituting said radicals may optionally be substituted by at least one radical selected from the group consisting of:

—$OR_4$,

—$SR_4$,

—$NR_4R_5$,

—$COOR_4$,

—$CONHR_4$,

—CN, a halogen atom, a $C_1$ to $C_6$ hydrofluoro- or perfluoroalkyl radical, a $C_3$ to $C_8$ cycloalkyl radical, and/or wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;

X is a radical selected from among the following:

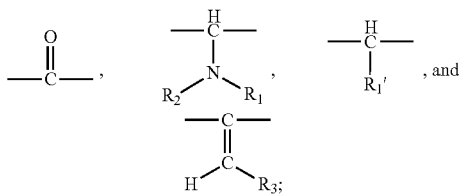

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;

S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and the S—CH$_2$—X bond is a bond of C-anomeric nature which can be α or β, and the cosmetically acceptable salts, solvates, hydrates and isomers thereof, wherein the condition requiring depigmenting/whitening the skin and/or for the anti-browning thereof is not aging.

2. A regime or regimen for lightening and/or whitening and/or rendering uniform the color of a browned skin, removing brownish blemishes and/or freckles, comprising topically administering to an area of hyperpigmentation on an individual in need of such treatment, for such period of time as required to elicit the desired response of lightening and/or whitening and/or rendering uniform the color of a browned skin, removing brownish pigment blemishes and/or freckles, a thus effective amount of at least one C-glycoside compound having the following formula (I):

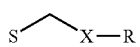 (I)

in which:
R is:
a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;
a saturated linear $C_1$ to $C_{20}$ hydrofluoro- or perfluoroalkyl radical, an unsaturated linear $C_2$ to $C_{20}$ hydrofluoro- or perfluoroalkyl radical or a saturated or unsaturated and branched or cyclic $C_3$ to $C_{20}$hydrofluoro- or perfluoroalkyl radical;
with the proviso that the hydrocarbon chain constituting said radicals may be interrupted by 1, 2, 3 or more heteroatoms selected from the group consisting of:
an oxygen atom,
a sulfur atom,
a nitrogen atom, and
a silicon atom,
and with the proviso that the hydrocarbon chain constituting said radicals may optionally be substituted by at least one radical selected from the group consisting of:
—OR$_4$,
—SR$_4$,
—NR$_4$R$_5$,
—COOR$_4$,
—CONHR$_4$,
—CN,
a halogen atom,
a $C_1$ to $C_6$ hydrofluoro- or perfluoroalkyl radical,
a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;

X is a radical selected from the group consisting of:

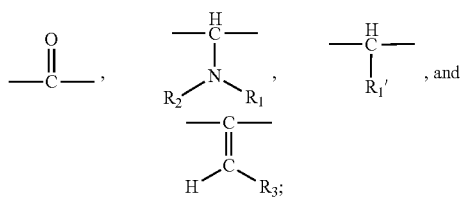

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;

S is a monosaccharide or a polysaccharide having up to 20 sugar units, in a pyranose and/or furanose form and of the L and/or D series, with the proviso that said mono- or polysaccharide may be substituted by a necessarily free hydroxyl group and optionally one or more optionally protected amine functional group(s), and the S—CH$_2$—X bond is a bond of C-anomeric nature which can be α or β, and the cosmetically acceptable salts, and the isomers thereof, wherein the condition requiring lightening and/or whitening and/or rendering uniform the color of a browned, removing brownish pigment blemishes and/or freckles is not aging.

3. A regime or regimen for depigmenting/whitening the skin and/or for the anti-browning thereof, comprising topically administering to an area of hyperpigmenation on an individual in need of such treatment, for such period of time as required to elicit the desired response of depigmenting/whitening the skin and/or for the anti-browning thereof, a thus effective amount of at least one C-glycoside compound having the following formula (I):

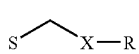 (I)

in which:
R is:
a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;
a saturated linear $C_1$ to $C_{20}$ hydrofluoro- or perfluoroalkyl radical, an unsaturated linear $C_2$ to $C_{20}$, in particular $C_2$ to $C_{10}$ hydrofluoro- or perfluoroalkyl radical or a saturated or unsaturated and branched or cyclic $C_3$ to $C_{20}$, hydrofluoro- or perfluoroalkyl radical;

with the proviso that the hydrocarbon chain constituting said radicals may be interrupted by 1, 2, 3 or more heteroatoms selected from the group consisting of:
an oxygen atom,
a sulfur atom,
a nitrogen atom, and
a silicon atom, and with the further proviso that the hydrocarbon chain constituting said radicals may optionally be substituted by at least one radical selected from the group consisting of:
—$OR_4$,
—$SR_4$,
—$NR_4R_5$,
—$COOR_4$,
—$CONHR_4$,
—CN,
a halogen atom,
a $C_1$ to $C_6$ hydrofluoro- or perfluoroalkyl radical,
a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;

X is a radical selected from the group consisting of:

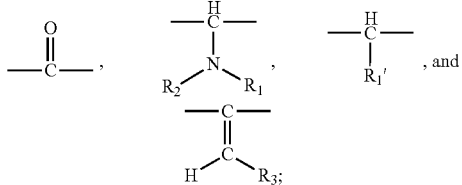

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;

S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and the S—$CH_2$—X bond is a bond of C-anomeric nature which can be α or β, and the cosmetically acceptable salts, and isomers thereof, wherein said individual is suffering from regional hyperpigmentations by melanocytic hyperactivity, post-inflammatory hyperpigmentation, accidental hyperpigmentations due to photosensitization or to post-lesional healing, and/or vitiligo.

4. The regime or regimen as defined by claim 1, said at least one C-glycoside compound being selected from the group consisting of:

(1) C-β-D-xylopyranoside-n-propan-2-one;
(2) C-α-D-xylopyranoside-n-propan-2-one;
(3) 1-[2-(3-hydroxypropylamino)propyl]-C-β-D-xylopyranose;
(4) 1-[2-(3-hydroxypropylamino)propyl]-C-α-D-xylopyranose;
(5) C-β-D-xylopyranoside-2-hydroxypropane;
(6) C-α-D-xylopyranoside-2-hydroxypropane;
(7) C-β-D-xylopyranoside-2-aminopropane;
(8) C-α-D-xylopyranoside-2-aminopropane;
(9) C-β-D-xylopyranoside-2-(phenylamino)propane;
(10) C-α-D-xylopyranoside-2-(phenylamino)propane;
(11) ethyl ester of 3-methyl-4-(C-β-D-xylopyranoside)butyric acid;
(12) ethyl ester of 3-methyl-4-(C-α-D-xylopyranoside)butyric acid;
(13) 6-(C-β-D-xylopyranoside)-5-ketohexanoic acid;
(14) 6-(C-α-D-xylopyranoside)-5-ketohexanoic acid;
(15) 6-(C-β-D-xylopyranoside)-5-hydroxyhexanoic acid;
(16) 6-(C-α-D-xylopyranoside)-5-hydroxyhexanoic acid;
(17) 6-(C-β-D-xylopyranoside)-5-aminohexanoic acid;
(18) 6-(C-α-D-xylopyranoside)-5-aminohexanoic acid;
(19) 6-(C-β-D-xylopyranoside)-5-(phenylamino)hexanoic acid;
(20) 6-(C-α-D-xylopyranoside)-5-(phenylamino)hexanoic acid;
(21) 1-(C-β-D-xylopyranoside)hexane-2,6-diol;
(22) 1-(C-α-D-xylopyranoside)hexane-2,6-diol;
(23) 5-(C-β-D-xylopyranoside)-4-ketopentanoic acid;
(24) 5-(C-α-D-xylopyranoside)-4-ketopentanoic acid;
(25) 5-(C-β-D-xylopyranoside)-4-hydroxypentanoic acid;
(26) 5-(C-α-D-xylopyranoside)-4-hydroxypentanoic acid;
(27) 5-(C-β-D-xylopyranoside)-4-aminopentanoic acid;
(28) 5-(C-α-D-xylopyranoside)-4-aminopentanoic acid;
(29) 5-(C-β-D-xylopyranoside)-4-(phenylamino)pentanoic acid;
(30) 5-(C-α-D-xylopyranoside)-4-(phenylamino)pentanoic acid;
(31) 1-(C-β-D-xylopyranoside)pentane-2,5-diol;
(32) 1-(C-α-D-xylopyranoside)pentane-2,5-diol;
(33) 1-(C-β-D-fucopyranoside)propan-2-one;
(34) 1-(C-α-D-fucopyranoside)propan-2-one;
(35) 1-(C-β-L-fucopyranoside)propan-2-one;
(36) 1-(C-α-L-fucopyranoside)propan-2-one;
(37) 1-(C-β-D-fucopyranoside)-2-hydroxypropane;
(38) 1-(C-α-D-fucopyranoside)-2-hydroxypropane;
(39) 1-(C-β-L-fucopyranoside)-2-hydroxypropane;
(40) 1-(C-α-L-fucopyranoside)-2-hydroxypropane;
(41) 1-(C-β-D-fucopyranoside)-2-aminopropane;
(42) 1-(C-α-D-fucopyranoside)-2-aminopropane;
(43) 1-(C-β-L-fucopyranoside)-2-aminopropane;
(44) 1-(C-α-L-fucopyranoside)-2-aminopropane;
(45) 1-(C-β-D-fucopyranoside)-2-(phenylamino)propane;
(46) 1-(C-α-D-fucopyranoside)-2-(phenylamino)propane;
(47) 1-(C-β-L-fucopyranoside)-2-(phenylamino)propane;
(48) 1-(C-α-L-fucopyranoside)-2-(phenylamino)propane;
(49) ethyl ester of 3-methyl-4-(C-β-D-fucopyranoside)butyric acid;
(50) ethyl ester of 3-methyl-4-(C-α-D-fucopyranoside)butyric acid;
(51) ethyl ester of 3-methyl-4-(C-β-L-fucopyranoside)butyric acid;
(52) ethyl ester of 3-methyl-4-(C-α-L-fucopyranoside)butyric acid;
(53) 6-(C-β-D-fucopyranoside)-5-ketohexanoic acid;
(54) 6-(C-α-D-fucopyranoside)-5-ketohexanoic acid;
(55) 6-(C-β-L-fucopyranoside)-5-ketohexanoic acid;
(56) 6-(C-α-L-fucopyranoside)-5-ketohexanoic acid;
(57) 6-(C-β-D-fucopyranoside)-5-hydroxyhexanoic acid;
(58) 6-(C-α-D-fucopyranoside)-5-hydroxyhexanoic acid;

(59) 6-(C-β-L-fucopyranoside)-5-hydroxyhexanoic acid;
(60) 6-(C-α-L-fucopyranoside)-5-hydroxyhexanoic acid;
(61) 6-(C-β-D-fucopyranoside)-5-aminohexanoic acid;
(62) 6-(C-α-D-fucopyranoside)-5-aminohexanoic acid;
(63) 6-(C-β-L-fucopyranoside)-5-aminohexanoic acid;
(64) 6-(C-α-L-fucopyranoside)-5-aminohexanoic acid;
(65) 1-(C-β-D-fucopyranoside)hexane-2,6-diol;
(66) 1-(C-α-D-fucopyranoside)hexane-2,6-diol;
(67) 1-(C-β-L-fucopyranoside)hexane-2,6-diol;
(68) 1-(C-α-L-fucopyranoside)hexane-2,6-diol;
(69) 5-(C-β-D-fucopyranoside)-4-ketopentanoic acid;
(70) 5-(C-α-D-fucopyranoside)-4-ketopentanoic acid;
(71) 5-(C-β-L-fucopyranoside)hexane-2,6-diol)-4-ketopentanoic acid;
(72) 5-(C-α-L-fucopyranoside)hexane-2,6-diol)-4-ketopentanoic acid;
(73) 5-(C-β-D-fucopyranoside)-4-hydroxypentanoic acid;
(74) 5-(C-α-D-fucopyranoside)-4-hydroxypentanoic acid;
(75) 5-(C-β-L-fucopyranoside)-4-hydroxypentanoic acid;
(76) 5-(C-α-L-fucopyranoside)-4-hydroxypentanoic acid;
(77) 5-(C-β-D-fucopyranoside)-4-aminopentanoic acid;
(78) 5-(C-α-D-fucopyranoside)-4-aminopentanoic acid;
(79) 5-(C-β-L-fucopyranoside)-4-aminopentanoic acid;
(80) 5-(C-α-L-fucopyranoside)-4-aminopentanoic acid;
(81) 1-(C-β-D-fucopyranoside)pentane-2,5-diol;
(82) 1-(C-α-D-fucopyranoside)pentane-2,5-diol;
(83) 1-(C-β-L-fucopyranoside)pentane-2,5-diol;
(84) 1-(C-α-L-fucopyranoside)pentane-2,5-diol;
(85) 1-(C-β-D-glucopyranosyl)-2-hydroxypropane;
(86) 1-(C-α-D-glucopyranosyl)-2-hydroxypropane;
(87) 1-(C-β-D-glucopyranosyl)-2-aminopropane;
(88) 1-(C-α-D-glucopyranosyl)-2-aminopropane;
(89) 1-(C-β-D-glucopyranosyl)-2-(phenylamino)propane;
(90) 1-(C-α-D-glucopyranosyl)-2-(phenylamino)propane;
(91) ethyl ester of 3-methyl-4-(C-β-D-glucopyranosyl)butyric acid;
(92) ethyl ester of 3-methyl-4-(C-α-D-glucopyranosyl)butyric acid;
(93) 6-(C-β-D-glucopyranosyl)-5-ketohexanoic acid;
(94) 6-(C-α-D-glucopyranosyl)-5-ketohexanoic acid;
(95) 6-(C-β-D-glucopyranosyl)-5-hydroxyhexanoic acid;
(96) 6-(C-α-D-glucopyranosyl)-5-hydroxyhexanoic acid;
(97) 6-(C-β-D-glucopyranosyl)-5-aminohexanoic acid;
(98) 6-(C-α-D-glucopyranosyl)-5-aminohexanoic acid;
(99) 6-(C-β-D-glucopyranosyl)-5-(phenylamino)hexanoic acid;
(100) 6-(C-α-D-glucopyranosyl)-5-(phenylamino)hexanoic acid;
(101) 1-(C-β-D-glucopyranosyl)hexane-2,6-diol;
(102) 1-(C-α-D-glucopyranosyl)hexane-2,6-diol;
(103) 6-(C-β-D-glucopyranosyl)-5-ketopentanoic acid;
(104) 6-(C-α-D-glucopyranosyl)-5-ketopentanoic acid;
(105) 6-(C-β-D-glucopyranosyl)-5-hydroxypentanoic acid;
(106) 6-(C-α-D-glucopyranosyl)-5-hydroxypentanoic acid;
(107) 6-(C-β-D-glucopyranosyl)-5-aminopentanoic acid;
(108) 6-(C-α-D-glucopyranosyl)-5-aminopentanoic acid;
(109) 6-(C-β-D-glucopyranosyl)-5-(phenylamino)pentanoic acid;
(110) 6-(C-α-D-glucopyranosyl)-5-(phenylamino)pentanoic acid;
(111) 1-(C-β-D-glucopyranosyl)pentane-2,5-diol;
(112) 1-(C-α-D-glucopyranosyl)pentane-2,5-diol;
(113) 1-(C-β-D-galactopyranosyl)-2-hydroxypropane;
(114) 1-(C-α-D-galactopyranosyl)-2-hydroxypropane;
(115) 1-(C-β-D-galactopyranosyl)-2-aminopropane;
(116) 1-(C-α-D-galactopyranosyl)-2-aminopropane;
(117) 1-(C-β-D-galactopyranosyl)-2-(phenylamino)propane;
(118) 1-(C-α-D-galactopyranosyl)-2-(phenylamino)propane;
(119) ethyl ester of 3-methyl-4-(C-β-D-galactopyranosyl)butyric acid;
(120) ethyl ester of 3-methyl-4-(C-α-D-galactopyranosyl)butyric acid;
(121) 6-(C-β-D-galactopyranosyl)-5-ketohexanoic acid;
(122) 6-(C-α-D-galactopyranosyl)-5-ketohexanoic acid;
(123) 6-(C-β-D-galactopyranosyl)-5-hydroxyhexanoic acid;
(124) 6-(C-α-D-galactopyranosyl)-5-hydroxyhexanoic acid;
(125) 6-(C-β-D-galactopyranosyl)-5-aminohexanoic acid;
(126) 6-(C-α-D-galactopyranosyl)-5-aminohexanoic acid;
(127) 6-(C-β-D-galactopyranosyl)-5-(phenylamino)hexanoic acid;
(128) 6-(C-α-D-galactopyranosyl)-5-(phenylamino)hexanoic acid;
(129) 1-(C-β-D-galactopyranosyl)hexane-2,6-diol;
(130) 1-(C-α-D-galactopyranosyl)hexane-2,6-diol;
(131) 6-(C-β-D-galactopyranosyl)-5-ketopentanoic acid;
(132) 6-(C-α-D-galactopyranosyl)-5-ketopentanoic acid;
(133) 6-(C-β-D-galactopyranosyl)-5-hydroxypentanoic acid;
(134) 6-(C-α-D-galactopyranosyl)-5-hydroxypentanoic acid;
(135) 6-(C-β-D-galactopyranosyl)-5-aminopentanoic acid;
(136) 6-(C-α-D-galactopyranosyl)-5-aminopentanoic acid;
(137) 6-(C-β-D-galactopyranosyl)-5-(phenylamino)pentanoic acid;
(138) 6-(C-α-D-galactopyranosyl)-5-(phenylamino)-pentanoic acid;
(139) 1-(C-β-D-galactopyranosyl)pentane-2,6-diol;
(140) 1-(C-α-D-galactopyranosyl)pentan-2,6-diol;
(141) 1-(C-β-D-fucofuranosyl)propan-2-one;
(142) 1-(C-α-D-fucofuranosyl)propan-2-one;
(143) 1-(C-β-L-fucofuranosyl)propan-2-one;
(144) 1-(C-α-L-fucofuranosyl)propan-2-one;
(145) 3'-(acetamido-C-β-D-glucopyranosyl)propan-2'-one;
(146) 3'-(acetamido-C-α-D-glucopyranosyl)propan-2'-one;
(147) 1-(C-β-D-galactopyranosyl)-2-hydroxypropane;
(148) 1-(C-α-D-galactopyranosyl)-2-aminopropane;
(149) 1-(acetamido-C-β-D-glucopyranosyl)-2-(phenylamino)propane;
(150) 1-(acetamido-C-α-D-glucopyranosyl)-2-(phenylamino)propane;
(151) ethyl ester of 3-methyl-4-(acetamido-C-β-D-glucopyranosyl)butyric acid;
(152) ethyl ester of 3-methyl-4-(acetamido-C-α-D-glucopyranosyl)butyric acid;
(153) 6-(acetamido-C-β-D-glucopyranosyl)-5-ketohexanoic acid;
(154) 6-(acetamido-C-α-D-glucopyranosyl)-5-ketohexanoic acid;
(155) 6-(acetamido-C-β-D-glucopyranosyl)-5-hydroxyhexanoic acid;
(156) 6-(acetamido-C-α-D-glucopyranosyl)-5-hydroxyhexanoic acid;

(157) 6-(acetamido-C-β-D-glucopyranosyl)-5-aminohexanoic acid;
(158) 6-(acetamido-C-α-D-glucopyranosyl)-5-aminohexanoic acid;
(159) 6-(acetamido-C-β-D-glucopyranosyl)-5-(phenylamino)hexanoic acid;
(160) 6-(acetamido-C-α-D-glucopyranosyl)-5-(phenylamino)-hexanoic acid;
(161) 1-(acetamido-C-β-D-glucopyranosyl)hexane-2,6-diol;
(162) 1-(acetamido-C-α-D-glucopyranosyl)hexane-2,6-diol;
(163) 6-(acetamido-C-β-D-glucopyranosyl)-5-ketopentanoic acid;
(164) 6-(acetamido-C-α-D-glucopyranosyl)-5-ketopentanoic acid;
(165) 6-(acetamido-C-β-D-glucopyranosyl)-5-hydroxypentanoic acid;
(166) 6-(acetamido-C-α-D-glucopyranosyl)-5-hydroxypentanoic acid;
(167) 6-(acetamido-C-β-D-glucopyranosyl)-5-aminopentanoic acid;
(168) 6-(acetamido-C-α-D-glucopyranosyl)-5-aminopentanoic acid;
(169) 6-(acetamido-C-β-D-glucopyranosyl)-5-(phenylamino)pentanoic acid;
(170) 6-(acetamido-C-α-D-glucopyranosyl)-5-(phenylamino)pentanoic acid;
(171) 1-(acetamido-C-β-D-glucopyranosyl)pentane-2,5-diol;
(172) 1-(acetamido-C-α-D-glucopyranosyl)pentane-2,5-diol; and mixtures thereof.

5. A regime or regimen for whitening the skin and/or scalp and/or mucous membranes, comprising topically administering to an area of hyperpigmenation on an individual in need of such treatment, for such period of time as required to elicit the desired response of whitening the skin and/or scalp and/or mucous membranes, a thus effective amount of at least one C-glycoside compound having the following formula (I):

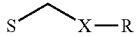

in which:
R is:
a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;
a saturated linear $C_1$ to $C_{20}$ hydrofluoro- or perfluoroalkyl radical, an unsaturated linear $C_2$ to $C_{20}$ hydrofluoro- or perfluoroalkyl radical or a saturated or unsaturated and branched or cyclic $C_3$ to $C_{20}$ hydrofluoro- or perfluoroalkyl radical;
with the proviso that the hydrocarbon chain constituting said radicals may be interrupted by 1, 2, 3 or more heteroatoms selected from the group consisting of:
an oxygen atom,
a sulfur atom,
a nitrogen atom, and
a silicon atom,
and with the proviso that the hydrocarbon chain consisting said radicals may optionally be substituted by at least one radical selected from the group consisting of:

—$OR_4$,
—$SR_4$,
—$NR_4R_5$,
—$COOR_4$,
—$CONHR_4$,
—CN,
a halogen atom,
a $C_1$ to $C_6$ hydrofluoro- or perfluoroalkyl radical,
a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;
X is a radical selected from the group consisting of:

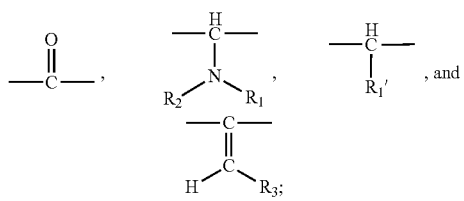

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;
S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and
the S—$CH_2$—X bond is a bond of C-anomeric nature which can be α or β, and the cosmetically acceptable salts, and the isomers thereof,
wherein the condition requiring whitening the skin and/or scalp and/or mucous membranes is not aging.

6. The regime or regimen of claim 1, where S is xylopyranoside.
7. The regime or regimen of claim 1, where X is —CH($R_1'$)—.
8. The regime or regimen of claim 7, where $R_1'$ is OH.
9. The regime or regimen of claim 1, where R is a saturated linear $C_1$ to $C_{10}$ alkyl radical.
10. The regime or regimen of claim 1, where R is a saturated linear $C_1$ to $C_4$ alkyl radical.
11. The regime or regimen of claim 1, where the at least one C-glycoside compound of formula (I) is C-β-D-xylopyranoside-2-hydroxypropane.
12. The regime or regimen of claim 2, where S is xylopyranoside.
13. The regime or regimen of claim 2, where X is —CH($R_1'$)—.
14. The regime or regimen of claim 13, where $R_1'$ is OH.
15. The regime or regimen of claim 2, where R is a saturated linear $C_1$ to $C_{10}$ alkyl radical.
16. The regime or regimen of claim 2, where R is a saturated linear $C_1$ to $C_4$ alkyl radical.

17. The regime or regimen of claim 2, where the at least one C-glycoside compound of formula (I) is C-β-D-xylopyranoside-2-hydroxypropane.

18. The regime or regimen of claim 5, where S is xylopyranoside.

19. The regime or regimen of claim 5, where X is —CH(R$_1$')—.

20. The regime or regimen of claim 19, where R$_1$' is OH.

21. The regime or regimen of claim 5, where R is a saturated linear C$_1$ to C$_{10}$ alkyl radical.

22. The regime or regimen of claim 5, where R is a saturated linear C$_1$ to C$_4$ alkyl radical.

23. The regime or regimen of claim 5, where the at least one C-glycoside compound of formula (I) is C-β-D-xylopyranoside-2-hydroxypropane.

24. The regime or regimen of claim 3, wherein said individual is suffering from regional hyperpigmentations caused by melanocytic hyperactivity selected from the group consisting of melasma of the forearms, idiopathic melasmas arising during pregnancy and idiopathic melasmas associated with oestrone/progestogen contraception.

25. A regime or regimen for depigmenting/whitening the skin and/or for the anti-browning thereof, comprising topically administering to an area surrounding an area of hyperdepigmenation on an individual in need of such treatment, for such period of time as required to elicit the desired response of depigmenting/whitening the skin and/or for the anti-browning thereof, a thus effective amount of at least one C-glycoside compound having the following formula (I):

$$S\diagdown{}\diagup{}X-R \qquad (I)$$

in which:
R is:
  a saturated linear C$_1$ to C$_{20}$ alkyl radical, an unsaturated linear C$_2$ to C$_{20}$ alkyl radical or a saturated or unsaturated and branched or cyclic C$_3$ to C$_{20}$ alkyl radical, with the exception of a substituted phenyl radical;
  a saturated linear C$_1$ to C$_{20}$ hydrofluoro- or perfluoroalkyl radical, an unsaturated linear C$_2$ to C$_{20}$, in particular C$_2$ to C$_{10}$, hydrofluoro- or perfluoroalkyl radical or a saturated or unsaturated and branched or cyclic C$_3$ to C$_{20}$, hydrofluoro- or perfluoroalkyl radical;
with the proviso that the hydrocarbon chain constituting said radicals may be interrupted by 1, 2, 3 or more heteroatoms selected from the group consisting of:
  an oxygen atom,
  a sulfur atom,
  a nitrogen atom, and
  a silicon atom,
and with the proviso that the hydrocarbon chain consisting said radicals may optionally be substituted by at least one radical selected from the group consisting of:
  —OR$_4$,
  —SR$_4$,
  —NR$_4$R$_5$,
  —COOR$_4$,
  —CONHR$_4$,
  —CN,
  a halogen atom,
  a C$_1$ to C$_6$ hydrofluoro- or perfluoroalkyl radical,
  a C$_3$ to C$_8$ cycloalkyl radical, and/or wherein R$_4$ and R$_5$ represent, independently of one another, a hydrogen atom, a saturated linear C$_1$ to C$_{30}$ alkyl, perfluoroalkyl or hydrofluoroalkyl radical, an unsaturated linear C$_2$ to C$_{30}$ alkyl, perfluoroalkyl or hydrofluoroalkyl radical, a saturated or unsaturated and branched or cyclic C$_3$ to C$_{30}$ alkyl, perfluoroalkyl or hydrofluoroalkyl radical, or a C$_6$ to C$_{10}$ aryl radical;

X is a radical selected from the group consisting of:

$$-\overset{O}{\underset{\|}{C}}-,\quad -\overset{H}{\underset{|}{\underset{N}{C}}}-,\quad -\overset{H}{\underset{|}{\underset{R_1'}{C}}}-,\quad \text{and}$$
$$\overset{}{\underset{R_2\diagup \;\;\diagdown R_1}{}}$$
$$-\overset{}{\underset{\underset{H\diagup \;\;\diagdown R_3}{\overset{\|}{C}}}{C}}-$$

wherein R$_1$, R$_2$ and R$_3$ represent, independently of one another, a hydrogen atom or a radical R, wherein R as defined above, and R'$_1$ is a hydrogen atom, an —OH group or a radical R, with the proviso that R$_1$ may also be a C$_6$ to C$_{10}$ aryl radical;

S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and the S—CH$_2$—X bond is a bond of C-anomeric nature which can be α or β, and the cosmetically acceptable salts, and isomers thereof, wherein the condition requiring depigmenting/whitening the skin and/or for the anti-browning thereof is not aging.

26. A regime or regimen for lightening and/or whitening and/or rendering uniform the color of a browned skin, removing brownish pigment blemishes and/or freckles, comprising topically administering to an area surrounding an area of hyperdepigmenation on an individual in need of such treatment, for such period of time as required to elicit the desired response of lightening and/or whitening and/or rendering uniform the color of a browned skin, removing brownish pigment blemishes and/or freckles, a thus effective amount of at least one C-glycoside compound having the following formula (I):

$$S\diagdown{}\diagup{}X-R \qquad (I)$$

in which:
R is:
  a saturated linear C$_1$ to C$_{20}$ alkyl radical, an unsaturated linear C$_2$ to C$_{20}$ alkyl radical or a saturated or unsaturated and branched or cyclic C$_3$ to C$_{20}$ alkyl radical, with the exception of a substituted phenyl radical;
  a saturated linear C$_1$ to C$_{20}$ hydrofluoro- or perfluoroalkyl radical, an unsaturated linear C$_2$ to C$_{20}$ hydrofluoro- or perfluoroalkyl radical or a saturated or unsaturated and branched or cyclic C$_3$ to C$_{20}$ hydrofluoro- or perfluoroalkyl radical; with the proviso that the hydrocarbon chain constituting said radicals may be interrupted by 1, 2, 3 or more heteroatoms selected from the group consisting of:

an oxygen atom,
a sulfur atom,
a nitrogen atom, and
a silicon atom,
and with the proviso that the hydrocarbon chain consisting said radicals may optionally be substituted by at least one radical selected from the group consisting of:
—$OR_4$,
—$SR_4$,
—$NR_4R_5$,
—$COOR_4$,
—$CONHR_4$,
—CN,
a halogen atom,
a $C_1$ to $C_6$ hydrofluoro- or perfluoroalkyl radical,
a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;

X is a radical selected from the group consisting of:

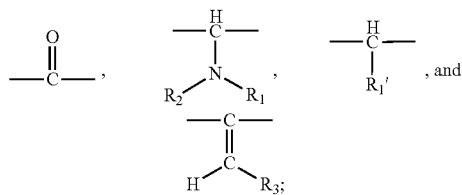

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;
  S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and
  the S—$CH_2$—X bond is a bond of C-anomeric nature which can be α or β and the cosmetically acceptable salts, and the isomers thereof,
wherein the condition requiring lightening and/or whitening and/or rendering uniform the color of a browned skin, removing brownish pigment blemishes and/or freckles is not aging.

27. A regime or regimen for depigmenting/whitening the skin and/or for the anti-browning thereof, comprising topically administering to an area surrounding an area of hyper-depigmentation on an individual in need of such treatment, for such period of time as required to elicit the desired response of depigmenting/whitening the skin and/or for the anti-browning thereof, a thus effective amount of at least one C-glycoside compound having the following formula (I):

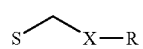

(I)

in which:
  R is:
    a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;
    a saturated linear $C_1$ to $C_{20}$ hydrofluoro- or perfluoroalkyl radical, an unsaturated linear $C_2$ to $C_{20}$, in particular $C_2$ to $C_{10}$, hydrofluoro- or perfluoroalkyl radical or a saturated or unsaturated and branched or cyclic $C_3$ to $C_{20}$, hydrofluoro- or perfluoroalkyl radical;
with the proviso that the hydrocarbon chain constituting said radicals may be interrupted by 1, 2, 3 or more heteroatoms selected from the group consisting of:
    an oxygen atom,
    a sulfur atom,
    a nitrogen atom, and
    a silicon atom,
and with the proviso that the hydrocarbon chain consisting said radicals may optionally be substituted by at least one radical selected from the group consisting of:
    —$OR_4$,
    —$SR_4$,
    —$NR_4R_5$,
    —$COOR_4$,
    —$CONHR_4$,
    —CN,
    a halogen atom,
    a $C_1$ to $C_6$ hydrofluoro- or perfluoroalkyl radical,
    a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;
X is a radical selected from the group consisting of:

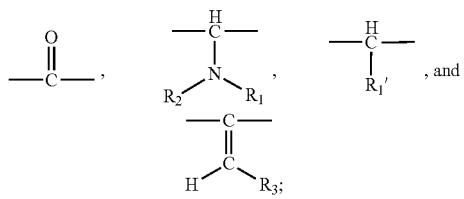

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;
  S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and
  the S—$CH_2$—X bond is a bond of C-anomeric nature which can be α or β, and the cosmetically acceptable salts, and isomers thereof,
wherein said individual is suffering from regional hyperpigmentations by melanocytic hyperactivity, post-inflammatory hyperpigmentation, accidental hyperpigmentations due to photosensitization or to post-lesional healing, and/or vitiligo.

28. The regime or regimen as defined by claim 25, said at least one C-glycoside compound being selected from the group consisting of:
(1) C-β-D-xylopyranoside-n-propan-2-one;
(2) C-α-D-xylopyranoside-n-propan-2-one;
(3) 1-[2-(3-hydroxypropylamino)propyl]-C-β-D-xylopyranose;
(4) 1-[2-(3-hydroxypropylamino)propyl]-C-α-D-xylopyranose;
(5) C-β-D-xylopyranoside-2-hydroxypropane;
(6) C-α-D-xylopyranoside-2-hydroxypropane;
(7) C-β-D-xylopyranoside-2-aminopropane;
(8) C-α-D-xylopyranoside-2-aminopropane;
(9) C-β-D-xylopyranoside-2-(phenylamino)propane;
(10) C-α-D-xylopyranoside-2-(phenylamino)propane;
(11) ethyl ester of 3-methyl-4-(C-β-D-xylopyranoside)butyric acid;
(12) ethyl ester of 3-methyl-4-(C-α-D-xylopyranoside)butyric acid;
(13) 6-(C-β-D-xylopyranoside)-5-ketohexanoic acid;
(14) 6-(C-α-D-xylopyranoside)-5-ketohexanoic acid;
(15) 6-(C-β-D-xylopyranoside)-5-hydroxyhexanoic acid;
(16) 6-(C-α-D-xylopyranoside)-5-hydroxyhexanoic acid;
(17) 6-(C-β-D-xylopyranoside)-5-aminohexanoic acid;
(18) 6-(C-α-D-xylopyranoside)-5-aminohexanoic acid;
(19) 6-(C-β-D-xylopyranoside)-5-(phenylamino)hexanoic acid;
(20) 6-(C-α-D-xylopyranoside)-5-(phenylamino)hexanoic acid;
(21) 1-(C-β-D-xylopyranoside)hexane-2,6-diol;
(22) 1-(C-α-D-xylopyranoside)hexane-2,6-diol;
(23) 5-(C-β-D-xylopyranoside)-4-ketopentanoic acid;
(24) 5-(C-α-D-xylopyranoside)-4-ketopentanoic acid;
(25) 5-(C-β-D-xylopyranoside)-4-hydroxypentanoic acid;
(26) 5-(C-α-D-xylopyranoside)-4-hydroxypentanoic acid;
(27) 5-(C-β-D-xylopyranoside)-4-aminopentanoic acid;
(28) 5-(C-α-D-xylopyranoside)-4-aminopentanoic acid;
(29) 5-(C-β-D-xylopyranoside)-4-(phenylamino)pentanoic acid;
(30) 5-(C-α-D-xylopyranoside)-4-(phenylamino)pentanoic acid;
(31) 1-(C-β-D-xylopyranoside)pentane-2,5-diol;
(32) 1-(C-α-D-xylopyranoside)pentane-2,5-diol;
(33) 1-(C-β-D-fucopyranoside)propan-2-one;
(34) 1-(C-α-D-fucopyranoside)propan-2-one;
(35) 1-(C-β-L-fucopyranoside)propan-2-one;
(36) 1-(C-α-L-fucopyranoside)propan-2-one;
(37) 1-(C-β-D-fucopyranoside)-2-hydroxypropane;
(38) 1-(C-α-D-fucopyranoside)-2-hydroxypropane;
(39) 1-(C-β-L-fucopyranoside)-2-hydroxypropane;
(40) 1-(C-α-L-fucopyranoside)-2-hydroxypropane;
(41) 1-(C-β-D-fucopyranoside)-2-aminopropane;
(42) 1-(C-α-D-fucopyranoside)-2-aminopropane;
(43) 1-(C-β-L-fucopyranoside)-2-aminopropane;
(44) 1-(C-α-L-fucopyranoside)-2-aminopropane;
(45) 1-(C-β-D-fucopyranoside)-2-(phenylamino)propane;
(46) 1-(C-α-D-fucopyranoside)-2-(phenylamino)propane;
(47) 1-(C-β-L-fucopyranoside)-2-(phenylamino)propane;
(48) 1-(C-α-L-fucopyranoside)-2-(phenylamino)propane;
(49) ethyl ester of 3-methyl-4-(C-β-D-fucopyranoside)butyric acid;
(50) ethyl ester of 3-methyl-4-(C-α-D-fucopyranoside)butyric acid;
(51) ethyl ester of 3-methyl-4-(C-β-L-fucopyranoside)butyric acid;
(52) ethyl ester of 3-methyl-4-(C-α-L-fucopyranoside)butyric acid;
(53) 6-(C-β-D-fucopyranoside)-5-ketohexanoic acid;
(54) 6-(C-α-D-fucopyranoside)-5-ketohexanoic acid;
(55) 6-(C-β-L-fucopyranoside)-5-ketohexanoic acid;
(56) 6-(C-α-L-fucopyranoside)-5-ketohexanoic acid;
(57) 6-(C-β-D-fucopyranoside)-5-hydroxyhexanoic acid;
(58) 6-(C-α-D-fucopyranoside)-5-hydroxyhexanoic acid;
(59) 6-(C-β-L-fucopyranoside)-5-hydroxyhexanoic acid;
(60) 6-(C-α-L-fucopyranoside)-5-hydroxyhexanoic acid;
(61) 6-(C-β-D-fucopyranoside)-5-aminohexanoic acid;
(62) 6-(C-α-D-fucopyranoside)-5-aminohexanoic acid;
(63) 6-(C-β-L-fucopyranoside)-5-aminohexanoic acid;
(64) 6-(C-α-L-fucopyranoside)-5-aminohexanoic acid;
(65) 1-(C-β-D-fucopyranoside)hexane-2,6-diol;
(66) 1-(C-α-D-fucopyranoside)hexane-2,6-diol;
(67) 1-(C-β-L-fucopyranoside)hexane-2,6-diol;
(68) 1-(C-α-L-fucopyranoside)hexane-2,6-diol;
(69) 5-(C-β-D-fucopyranoside)-4-ketopentanoic acid;
(70) 5-(C-α-D-fucopyranoside)-4-ketopentanoic acid;
(71) 5-(C-β-L-fucopyranoside)hexane-2,6-diol)-4-ketopentanoic acid;
(72) 5-(C-α-L-fucopyranoside)hexane-2,6-diol)-4-ketopentanoic acid;
(73) 5-(C-β-D-fucopyranoside)-4-hydroxypentanoic acid;
(74) 5-(C-α-D-fucopyranoside)-4-hydroxypentanoic acid;
(75) 5-(C-β-L-fucopyranoside)-4-hydroxypentanoic acid;
(76) 5-(C-α-L-fucopyranoside)-4-hydroxypentanoic acid;
(77) 5-(C-β-D-fucopyranoside)-4-aminopentanoic acid;
(78) 5-(C-α-D-fucopyranoside)-4-aminopentanoic acid;
(79) 5-(C-β-L-fucopyranoside)-4-aminopentanoic acid;
(80) 5-(C-α-L-fucopyranoside)-4-aminopentanoic acid;
(81) 1-(C-β-D-fucopyranoside)pentane-2,5-diol;
(82) 1-(C-α-D-fucopyranoside)pentane-2,5-diol;
(83) 1-(C-β-L-fucopyranoside)pentane-2,5-diol;
(84) 1-(C-α-L-fucopyranoside)pentane-2,5-diol;
(85) 1-(C-β-D-glucopyranosyl)-2-hydroxypropane;
(86) 1-(C-α-D-glucopyranosyl)-2-hydroxypropane;
(87) 1-(C-β-D-glucopyranosyl)-2-aminopropane;
(88) 1-(C-α-D-glucopyranosyl)-2-aminopropane;
(89) 1-(C-β-D-glucopyranosyl)-2-(phenylamino)propane;
(90) 1-(C-α-D-glucopyranosyl)-2-(phenylamino)propane;
(91) ethyl ester of 3-methyl-4-(C-β-D-glucopyranosyl)butyric acid;
(92) ethyl ester of 3-methyl-4-(C-α-D-glucopyranosyl)butyric acid;
(93) 6-(C-β-D-glucopyranosyl)-5-ketohexanoic acid;
(94) 6-(C-α-D-glucopyranosyl)-5-ketohexanoic acid;
(95) 6-(C-β-D-glucopyranosyl)-5-hydroxyhexanoic acid;
(96) 6-(C-α-D-glucopyranosyl)-5-hydroxyhexanoic acid;
(97) 6-(C-β-D-glucopyranosyl)-5-aminohexanoic acid;
(98) 6-(C-α-D-glucopyranosyl)-5-aminohexanoic acid;
(99) 6-(C-β-D-glucopyranosyl)-5-(phenylamino)hexanoic acid;
(100) 6-(C-α-D-glucopyranosyl)-5-(phenylamino)hexanoic acid;
(101) 1-(C-β-D-glucopyranosyl)hexane-2,6-diol;
(102) 1-(C-α-D-glucopyranosyl)hexane-2,6-diol;
(103) 6-(C-β-D-glucopyranosyl)-5-ketopentanoic acid;
(104) 6-(C-α-D-glucopyranosyl)-5-ketopentanoic acid;
(105) 6-(C-β-D-glucopyranosyl)-5-hydroxypentanoic acid;
(106) 6-(C-α-D-glucopyranosyl)-5-hydroxypentanoic acid;

(107) 6-(C-β-D-glucopyranosyl)-5-aminopentanoic acid;
(108) 6-(C-α-D-glucopyranosyl)-5-aminopentanoic acid;
(109) 6-(C-β-D-glucopyranosyl)-5-(phenylamino)pentanoic acid;
(110) 6-(C-α-D-glucopyranosyl)-5-(phenylamino)pentanoic acid;
(111) 1-(C-β-D-glucopyranosyl)pentane-2,5-diol;
(112) 1-(C-α-D-glucopyranosyl)pentane-2,5-diol;
(113) 1-(C-β-D-galactopyranosyl)-2-hydroxypropane;
(114) 1-(C-α-D-galactopyranosyl)-2-hydroxypropane;
(115) 1-(C-β-D-galactopyranosyl)-2-aminopropane;
(116) 1-(C-α-D-galactopyranosyl)-2-aminopropane;
(117) 1-(C-β-D-galactopyranosyl)-2-(phenylamino)propane;
(118) 1-(C-α-D-galactopyranosyl)-2-(phenylamino)propane;
(119) ethyl ester of 3-methyl-4-(C-β-D-galactopyranosyl)butyric acid;
(120) ethyl ester of 3-methyl-4-(C-α-D-galactopyranosyl)butyric acid;
(121) 6-(C-β-D-galactopyranosyl)-5-ketohexanoic acid;
(122) 6-(C-α-D-galactopyranosyl)-5-ketohexanoic acid;
(123) 6-(C-β-D-galactopyranosyl)-5-hydroxyhexanoic acid;
(124) 6-(C-α-D-galactopyranosyl)-5-hydroxyhexanoic acid;
(125) 6-(C-β-D-galactopyranosyl)-5-aminohexanoic acid;
(126) 6-(C-α-D-galactopyranosyl)-5-aminohexanoic acid;
(127) 6-(C-β-D-galactopyranosyl)-5-(phenylamino)hexanoic acid;
(128) 6-(C-α-D-galactopyranosyl)-5-(phenylamino)hexanoic acid;
(129) 1-(C-β-D-galactopyranosyl)hexane-2,6-diol;
(130) 1-(C-α-D-galactopyranosyl)hexane-2,6-diol;
(131) 6-(C-β-D-galactopyranosyl)-5-ketopentanoic acid;
(132) 6-(C-α-D-galactopyranosyl)-5-ketopentanoic acid;
(133) 6-(C-β-D-galactopyranosyl)-5-hydroxypentanoic acid;
(134) 6-(C-α-D-galactopyranosyl)-5-hydroxypentanoic acid;
(135) 6-(C-β-D-galactopyranosyl)-5-aminopentanoic acid;
(136) 6-(C-α-D-galactopyranosyl)-5-aminopentanoic acid;
(137) 6-(C-β-D-galactopyranosyl)-5-(phenylamino)pentanoic acid;
(138) 6-(C-α-D-galactopyranosyl)-5-(phenylamino)-pentanoic acid;
(139) 1-(C-β-D-galactopyranosyl)pentane-2,6-diol;
(140) 1-(C-α-D-galactopyranosyl)pentan-2,6-diol;
(141) 1-(C-β-D-fucofuranosyl)propan-2-one;
(142) 1-(C-α-D-fucofuranosyl)propan-2-one;
(143) 1-(C-β-L-fucofuranosyl)propan-2-one;
(144) 1-(C-α-L-fucofuranosyl)propan-2-one;
(145) 3'-(acetamido-C-β-D-glucopyranosyl)propan-2'-one;
(146) 3'-(acetamido-C-α-D-glucopyranosyl)propan-2'-one;
(147) 1-(C-β-D-galactopyranosyl)-2-hydroxypropane;
(148) 1-(C-α-D-galactopyranosyl)-2-aminopropane;
(149) 1-(acetamido-C-β-D-glucopyranosyl)-2-(phenylamino)propane;
(150) 1-(acetamido-C-α-D-glucopyranosyl)-2-(phenylamino)propane;
(151) ethyl ester of 3-methyl-4-(acetamido-C-β-D-glucopyranosyl)butyric acid;
(152) ethyl ester of 3-methyl-4-(acetamido-C-α-D-glucopyranosyl)butyric acid;
(153) 6-(acetamido-C-β-D-glucopyranosyl)-5-ketohexanoic acid;
(154) 6-(acetamido-C-α-D-glucopyranosyl)-5-ketohexanoic acid;
(155) 6-(acetamido-C-β-D-glucopyranosyl)-5-hydroxyhexanoic acid;
(156) 6-(acetamido-C-α-D-glucopyranosyl)-5-hydroxyhexanoic acid;
(157) 6-(acetamido-C-β-D-glucopyranosyl)-5-aminohexanoic acid;
(158) 6-(acetamido-C-α-D-glucopyranosyl)-5-aminohexanoic acid;
(159) 6-(acetamido-C-β-D-glucopyranosyl)-5-(phenylamino)hexanoic acid;
(160) 6-(acetamido-C-α-D-glucopyranosyl)-5-(phenylamino)-hexanoic acid;
(161) 1-(acetamido-C-β-D-glucopyranosyl)hexane-2,6-diol;
(162) 1-(acetamido-C-α-D-glucopyranosyl)hexane-2,6-diol;
(163) 6-(acetamido-C-β-D-glucopyranosyl)-5-ketopentanoic acid;
(164) 6-(acetamido-C-α-D-glucopyranosyl)-5-ketopentanoic acid;
(165) 6-(acetamido-C-β-D-glucopyranosyl)-5-hydroxypentanoic acid;
(166) 6-(acetamido-C-α-D-glucopyranosyl)-5-hydroxypentanoic acid;
(167) 6-(acetamido-C-β-D-glucopyranosyl)-5-aminopentanoic acid;
(168) 6-(acetamido-C-α-D-glucopyranosyl)-5-aminopentanoic acid;
(169) 6-(acetamido-C-β-D-glucopyranosyl)-5-(phenylamino)pentanoic acid;
(170) 6-(acetamido-C-α-D-glucopyranosyl)-5-(phenylamino)pentanoic acid;
(171) 1-(acetamido-C-β-D-glucopyranosyl)pentane-2,5-diol;
(172) 1-(acetamido-C-α-D-glucopyranosyl)pentane-2,5-diol; and mixtures thereof.

29. A regime or regimen for whitening the skin and/or scalp and/or mucous membranes, comprising topically administering to an area surrounding an area of hyperdepigmenation on an individual in need of such treatment, for such period of time as required to elicit the desired response of whitening the skin and/or scalp and/or mucous membranes, a thus effective amount of at least one C-glycoside compound having the following formula (I):

in which:
R is:
a saturated linear $C_1$ to $C_{20}$ alkyl radical, an unsaturated linear $C_2$ to $C_{20}$ alkyl radical or a saturated or unsaturated and branched or cyclic $C_3$ to $C_{20}$ alkyl radical, with the exception of a substituted phenyl radical;
a saturated linear $C_1$ to $C_{20}$ hydrofluoro- or perfluoroalkyl radical, an unsaturated linear $C_2$ to $C_{20}$ hydrofluoro- or perfluoroalkyl radical or a saturated or unsaturated and branched or cyclic $C_3$ to $C_{20}$ hydrofluoro- or perfluoroalkyl radical;

with the proviso that the hydrocarbon chain constituting said radicals may be interrupted by 1, 2, 3 or more heteroatoms selected from the group consisting of:
an oxygen atom,
a sulfur atom,
a nitrogen atom, and
a silicon atom,
and with the proviso that the hydrocarbon chain consisting said radicals may optionally be substituted by at least one radical selected from the group consisting of:
—$OR_4$,
—$SR_4$,
—$NR_4R_5$,
—$COOR_4$,
—$CONHR_4$,
—CN,
a halogen atom,
a $C_1$ to $C_6$ hydrofluoro- or perfluoroalkyl radical,
a $C_3$ to $C_8$ cycloalkyl radical, and/or
wherein $R_4$ and $R_5$ represent, independently of one another, a hydrogen atom, a saturated linear $C_1$ to $C_{30}$ alkyl, perfluoroalkyl or hydrofluoroalkyl radical, an unsaturated linear $C_2$ to $C_{30}$ alkyl, perfluoroalkyl or hydrofluoroalkyl radical, a saturated or unsaturated and branched or cyclic $C_3$ to $C_{30}$ alkyl, perfluoroalkyl or hydrofluoroalkyl radical, or a $C_6$ to $C_{10}$ aryl radical;

X is a radical selected from the group consisting of:

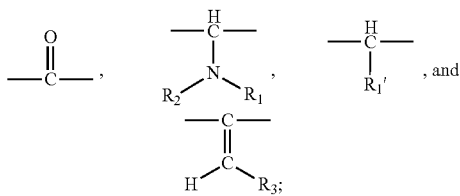

wherein $R_1$, $R_2$ and $R_3$ represent, independently of one another, a hydrogen atom or a radical R, wherein R as defined above, and $R'_1$ is a hydrogen atom, an —OH group or a radical R, with the proviso that $R_1$ may also be a $C_6$ to $C_{10}$ aryl radical;

S is a monosaccharide or a polysaccharide having up to 20 sugar units in a pyranose and/or furanose form and of the L and/or D series, with the proviso that said mono- or polysaccharide may be substituted by a necessarily free hydroxyl group and optionally one or more optionally protected amine functional group(s), and the S—$CH_2$—X bond is a bond of C-anomeric nature which can be α or β, and the cosmetically acceptable salts, and the isomers thereof, wherein the condition requiring whitening the skin and/or scalp and/or mucous membranes is not aging.

30. The regime or regimen of claim 25, where S is xylopyranoside.

31. The regime or regimen of claim 25, where X is —CH($R_1'$)—.

32. The regime or regimen of claim 31, where $R_1'$ is OH.

33. The regime or regimen of claim 25, where R is a saturated linear $C_1$ to $C_{10}$ alkyl radical.

34. The regime or regimen of claim 25, where R is a saturated linear $C_1$ to $C_4$ alkyl radical.

35. The regime or regimen of claim 25, where the at least one C-glycoside compound of formula (I) is C-β-D-xylopyranoside-2-hydroxypropane.

36. The regime or regimen of claim 26, where S is xylopyranoside.

37. The regime or regimen of claim 26, where X is —CH($R_1'$)—.

38. The regime or regimen of claim 37, where $R_1'$ is OH.

39. The regime or regimen of claim 26, where R is a saturated linear $C_1$ to $C_{10}$ alkyl radical.

40. The regime or regimen of claim 26, where R is a saturated linear $C_1$ to $C_4$ alkyl radical.

41. The regime or regimen of claim 26, where the at least one C-glycoside compound of formula (I) is C-β-D-xylopyranoside-2-hydroxypropane.

42. The regime or regimen of claim 29, where S is xylopyranoside.

43. The regime or regimen of claim 5, where X is —CH($R_1'$)—.

44. The regime or regimen of claim 43, where $R_1'$ is OH.

45. The regime or regimen of claim 29, where R is a saturated linear $C_1$ to $C_{10}$ alkyl radical.

46. The regime or regimen of claim 29, where R is a saturated linear $C_1$ to $C_4$ alkyl radical.

47. The regime or regimen of claim 29, where the at least one C-glycoside compound of formula (I) is C-β-D-xylopyranoside-2-hydroxypropane.

* * * * *